United States Patent
Yamano et al.

(10) Patent No.: US 7,852,349 B2
(45) Date of Patent: Dec. 14, 2010

(54) IMAGE DISPLAY METHOD AND IMAGE DISPLAY APPARATUS

(75) Inventors: Akira Yamano, Hino (JP); Masayuki Nakazawa, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 805 days.

(21) Appl. No.: 11/888,023

(22) Filed: Jul. 31, 2007

(65) Prior Publication Data

US 2008/0089572 A1 Apr. 17, 2008

(30) Foreign Application Priority Data

Aug. 4, 2006 (JP) ............................... 2006-213129

(51) Int. Cl.
| | |
|---|---|
| G09G 5/00 | (2006.01) |
| G09G 5/02 | (2006.01) |
| G09G 5/36 | (2006.01) |
| G06K 9/00 | (2006.01) |
| G06K 9/40 | (2006.01) |
| G03F 3/08 | (2006.01) |
| H04N 5/00 | (2006.01) |
| H04N 5/04 | (2006.01) |
| H04N 9/04 | (2006.01) |
| H04N 1/46 | (2006.01) |
| G06K 9/32 | (2006.01) |

(52) U.S. Cl. ........................ 345/600; 345/589; 345/593; 345/204; 345/690; 348/277; 348/502; 348/612; 358/518; 358/519; 358/523; 382/162; 382/167; 382/274; 382/276

(58) Field of Classification Search .................. 345/22, 345/88–89, 204, 581, 589, 600–606, 593, 345/690, 643–644; 348/253–254, 263, 277, 348/498, 502, 557, 612, 716–717; 382/162–167, 382/169, 254, 274, 276; 358/518–520, 523–525, 358/447–448

See application file for complete search history.

(56) References Cited

U.S. PATENT DOCUMENTS 5,258,747 A * 11/1993 Oda et al. .................... 345/602

(Continued)

FOREIGN PATENT DOCUMENTS

JP        2000-330530 A    11/2000

(Continued)

Primary Examiner—Wesner Sajous
(74) Attorney, Agent, or Firm—Holtz, Holtz, Goodman & Chick, PC

(57) ABSTRACT

There is described an image display apparatus that includes an image data processing section to convert (n+m)-bit monochromatic image data to a n-bit color display image-data group, based on a predetermined correlation, and a color image display section to display a color image on it, based on the n-bit color display image-data group. The image data processing section includes: a candidate selection section to select "H" sets of signal-values out of all combinations of signal-values included in the n-bit color display image-data group as the candidate color display signal-value sets; a signal value decision section to determine a color display signal-value set, to be correlated with the (n+m)-bit monochromatic image data, from among the "H" sets of candidate color display signal-value sets; and a correlation establishing section to establish the correlation between the (n+m)-bit monochromatic image data and the n-bit color display image-data group.

28 Claims, 11 Drawing Sheets

U.S. PATENT DOCUMENTS

| | | | |
|---|---|---|---|
| 5,619,227 A * | 4/1997 | Takebe | 345/690 |
| 5,712,651 A * | 1/1998 | Tomiyasu | 345/88 |
| 2004/0140972 A1* | 7/2004 | Hirota et al. | 345/204 |

FOREIGN PATENT DOCUMENTS

| | | |
|---|---|---|
| JP | 2001-034232 A | 2/2001 |
| JP | 2003-050566 A | 2/2003 |

* cited by examiner

TABLE A

| INTERNAL SIGNAL VALUE | TEST PATTERN SIGNAL VALUE | | | MEASURED LUMINANCE |
|---|---|---|---|---|
| | R | G | B | Y |
| 0 | 0 | 0 | 0 | Ymin |
| 273 | 17 | 17 | 17 | ⋮ |
| 456 | 34 | 34 | 34 | ⋮ |
| 819 | 51 | 51 | 51 | ⋮ |
| 1092 | 68 | 68 | 68 | ⋮ |
| 1365 | 65 | 65 | 65 | ⋮ |
| 1638 | 102 | 102 | 102 | ⋮ |
| 1911 | 119 | 119 | 119 | ⋮ |
| 2184 | 136 | 136 | 136 | ⋮ |
| 2457 | 153 | 153 | 153 | ⋮ |
| 2730 | 170 | 170 | 170 | ⋮ |
| 3003 | 187 | 187 | 187 | ⋮ |
| 3276 | 204 | 204 | 204 | ⋮ |
| 3549 | 221 | 221 | 221 | ⋮ |
| 3822 | 238 | 238 | 238 | ⋮ |
| 4095 | 255 | 255 | 255 | Ymax |

TABLE B

| INTERNAL SIGNAL VALUE | ESTIMATED MEASURED LUMINANCE Y |
|---|---|
| 0 | Ymin |
| 1 | ⋮ |
| 2 | ⋮ |
| 3 | ⋮ |
| 4 | ⋮ |
| ⋮ | ⋮ |
| 2045 | ⋮ |
| 2046 | ⋮ |
| 2047 | ⋮ |
| 2048 | ⋮ |
| ⋮ | ⋮ |
| 4091 | ⋮ |
| 4092 | ⋮ |
| 4093 | ⋮ |
| 4094 | ⋮ |
| 4095 | Ymax |

=

⊗

IMAGE DISPLAY METHOD AND IMAGE DISPLAY APPARATUS

This application is based on Japanese Patent Application No. 2006-213129 filed on Aug. 4, 2006 with Japan Patent Office, the entire content of which is hereby incorporated by reference.

BACKGROUND OF THE INVENTION

The present invention relates to an image display method and an image display apparatus and more particularly to an image display method and an image display apparatus for displaying on a color display a monochromatic image having grayscales larger in number than the drive grayscales of the image display section.

A diagnostic image picked up by a medical diagnostic apparatus such as an X-ray diagnostic apparatus, an MRI (magnetic resonance imaging) diagnostic apparatus, or various CT (computed tomography) apparatuses is generally recorded on a light transmissible image recording film such as an X-ray film or other film photosensitive materials and is reproduced as a light transmissible image. The film on which the diagnostic image is reproduced is set in an observation apparatus called a viewing box, is observed in a state that light is irradiated from the rear thereof, and is diagnosed of existence of a lesion.

Further, to various medical diagnostic and measuring apparatuses, as a monitor for observing a picked-up and measured image, a color display such as a CRT (cathode ray tube) display or an LCD (liquid crystal display) is connected and by images outputted to these display screens, a diagnosis, confirmation and adjustment of a diagnostic image before outputted to the film, and an image process are performed.

Meanwhile, when reproducing the image picked up by the aforementioned X-ray diagnostic apparatus on a film, generally, a blue-based monochromatic film is used often. Further, generally, an image is reproduced often by a grayscale resolution 10 to 12 bits long (1024 to 4096 grayscales).

Therefore, also when diagnosing an image on a display such as a CRT or an LCD, an exclusive monochromatic display having a grayscale resolution more than 10 bits long is used often.

On the other hands, to display a color image by an endoscope or an eyeground camera, a color display is used. Further, in recent years, also when displaying a three-dimensional image by an ultrasound diagnostic apparatus, a CT apparatus, or an MRI apparatus, a color display has been used.

To make a synthetic diagnosis, it is necessary to observe images of a plurality of kinds of diagnostic apparatuses and for that purpose, both exclusive high-grayscale monochromatic and color displays must be installed and a problem arises that it is expensive and a wide installation space is required.

A color display can display a monochromatic (black and white) image, though on the color display, an image is displayed generally at an 8-bit grayscale resolution, so that when reproducing an image on an ordinary display screen, an image is displayed by the so-called bit-down image data having a lower grayscale resolution than that of an image picked-up and outputted by the aforementioned X-ray diagnostic apparatus.

Concretely, for example, to convert 10-bit monochromatic image data to 8-bit R, G, and B image data, a monochromatic image signal value of 1024 grayscales, on the basis of an LUT (look up table) as shown in FIG. 19, is converted to R, G, and B values of 256 grayscales. Here, in the conventional LUT, the R, G, and B values are all equivalent and a problem arises that the R, G, and B image data cannot display an image of grayscales more than 256 grayscales.

Furthermore, as in the invention described in Patent Document 1 (Tokkai 2000-330530, Japanese Non-Examined Patent Publication), an image display apparatus for making the B value in the LUT larger than the R and G values, thereby reproducing a blue-based monochromatic film is known. According to such an image display apparatus, an LUT is prepared under the condition of R value=G value=K×B value (0<K<1), thus the color tone of the blue-based monochromatic film can be reproduced almost, though the maximum values of the R and G values become smaller than 256, so that the number of displayable grayscales becomes smaller than 256, thus when reproducing the color tone of the blue-based monochromatic film, the reduction in the number of grayscales is a bigger problem.

As a method for displaying grayscales more than the number of drive grayscales of the display, a method of FRC (frame rate control) display is devised.

Here, the FRC display device that when displaying image data having a high grayscale resolution (the number of bits) as image data having a low grayscale resolution (the number of bits), from the image data having a large number of bits, image data having a small number of bits which is the number of bits in accordance with the difference in the number of bits between both image data is prepared, and the image data is displayed sequentially, thus a grayscale equivalent to the large number of bits is represented by image display of the small number of bits.

Concretely, assuming the difference in the number of bits as n, image data of a small number of bits of the number of frames $2^n$ is prepared, and the image data of the small number of bits is displayed sequentially, thus for example, using 4 frames of images of an 8-bit grayscale resolution, a grayscale equivalent to a 10-bit grayscale resolution is represented.

Further, as in the invention described in Patent Document 2 (Tokkai 2001-034232, Japanese Non-Examined Patent Publication), an LUT is prepared so that not only the R, G, and B values are equivalent but also as shown in Table 1 of Patent Document 2, the R, G, and B values are not reduced monotonously and the total of the R, G, and B values is changed one by one, thus an image of 765 grayscales can be displayed.

Furthermore, as in the invention described in Patent Document 3 (Tokkai 2003-050566, Japanese Non-Examined Patent Publication), an image display apparatus for representing a multi-grayscale using an LUT for changing a sub-pixel signal value within an optional range is known. According to such an image display, theoretically, an image of 4096 or more grayscales can be displayed.

However, in the FRC display, a problem arises that image flickering which is called the so-called flicker is conspicuous and the eyes are made tired and another problem arises that the burden imposed on the process required to change the divided display data in the FRC representation is great.

Further, in the image display apparatus described in Patent Document 2, the maximum value of an input monochromatic image signal value is converted to the "maximum value of R+maximum value of G+maximum value of B", and the R, G, and B signal values are divided and distributed almost evenly, and the restriction to the combination of the R, G, and B values is strict, so that unless the FRC display is performed, only an image of 766 grayscales is represented, thus the image display apparatus is insufficient to a simple pick-up image diagnosis.

Furthermore, in the image display apparatus described in Patent Document 3, a multi-grayscale display on a monochromatic monitor is supposed, so that the selectable range of a sub-pixel signal value is excessively large and the sub-pixel signal value is selected only under the condition concerning luminance, thus even if a monochromatic image is displayed on a color monitor using a prepared LUT, a problem arises that it cannot be displayed with a color tone suited to diagnosis. Further, it is described that the image display apparatus described in Patent Document 3 can be applied also to the color monitor, though in that case, the pixels of R, G, and B must be divided furthermore into sub-pixels and a problem arises that the constitution is complicated.

SUMMARY OF THE INVENTION

To overcome the abovementioned drawbacks in conventional image display methods, it is one of objects of the present invention to provide an image display method and an image display apparatus, which make it possible not only to display a monochromatic image, having an appropriate color tone, on a color display, but also to represent a multi-grayscale image having a number of gradations, which is equal to or greater than four times of the number of drive grayscales of the color display, without employing the FRC display mode.

Accordingly, at least one of abovementioned objects of the present invention can be attained by the image display methods and the image display apparatuses described as follows.

(1) According to an image display method reflecting an aspect of the present invention, the image display method for displaying an image on a color monitor, based on a n-bit color display image-data group that is represented by plural channels including three channels or more, and that is acquired by converting (n+m)-bit monochromatic image data represented by a single channel to the n-bit color display image-data group, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2, the image display method comprises: selecting "H" sets of signal-values of the plural channels out of all combinations of signal-values of the plural channels included in the n-bit color display image-data group as candidate color display signal-value sets, wherein numeral "H" indicates a positive integer; determining a single color display signal-value set, to be correlated with each of signal values represented by the (n+m)-bit monochromatic image data, from among the "H" sets of candidate color display signal-value sets, with respect to each of the signal values represented by the (n+m)-bit monochromatic image data; and establishing the correlation by correlating each of the signal values represented by the (n+m)-bit monochromatic image data with the color display signal-value set determined in the determining step while corresponding thereto.

(2) According to another aspect of the present invention, in the image display method recited in item 1, numeral "H", being a number of the candidate color display signal-value sets, fulfills equations indicated as follows;

$H = C \times 2^n$ $2^{(m+1)} \leq C \leq 2^{(m+4)}$.

(3) According to another aspect of the present invention, the image display method, recited in item 1 or 2, further comprises: acquiring luminance information corresponding to each of the signal values represented by the (n+m)-bit monochromatic image data; acquiring chromaticity information corresponding to each of the signal values represented by the (n+m)-bit monochromatic image data; wherein, in the determining step, the single color display signal-value set, which is correlated with each of the signal values represented by the (n+m)-bit monochromatic image data, is determined, based on the luminance information and the chromaticity information acquired in the acquiring steps.

(4) According to still another aspect of the present invention, in the image display method recited in item 1 or 2, the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

(5) According to yet another aspect of the present invention, the image display method, recited in item 1 or 2, further comprises: selecting a desired color tone of the image to be displayed on the color monitor from a plurality of candidate color tones; wherein the candidate color display signal-value sets are selected, so that the desired color tone corresponds to a color tone of the image to be displayed on the color monitor.

(6) According to an image display method reflecting another aspect of the present invention, the image display method for displaying an image on a color monitor, based on a n-bit color display image-data group that is represented by plural channels including three channels or more, and that is acquired by converting (n+m)-bit monochromatic image data represented by a single channel to the n-bit color display image-data group, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2, the image display method comprising: selecting "H" sets of signal-values of the plural channels out of all combinations of signal-values of the plural channels included in the n-bit color display image-data group as candidate color display signal-value sets, wherein numeral "H" indicates a positive integer; acquiring luminance information corresponding to each of the signal values represented by the (n+m)-bit monochromatic image data; determining a single color display signal-value set, to be correlated with each of signal values represented by the (n+m)-bit monochromatic image data, from among the "H" sets of candidate color display signal-value sets, based on the luminance information, with respect to each of the signal values represented by the (n+m)-bit monochromatic image data; and establishing the correlation by correlating each of the signal values represented by the (n+m)-bit monochromatic image data with the color display signal-value set determined in the determining step while corresponding thereto.

(7) According to another aspect of the present invention, in the image display method recited in item 6, numeral "H", being a number of the candidate color display signal-value sets, fulfills equations indicated as follows;

$H = C \times 2^n$ $2^{(m+1)} \leq C \leq 2^{(m+3)}$.

(8) According to still another aspect of the present invention, in the image display method recited in item 6 or 7, the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

(9) According to yet another aspect of the present invention, the image display method, recited in item 6 or 7, further comprises: selecting a desired color tone of the image to be displayed on the color monitor from a plurality of candidate color tones; wherein the candidate color display signal-value sets are selected, so that the desired color tone corresponds to a color tone of the image to be displayed on the color monitor.

(10) According to an image display apparatus reflecting still another aspect of the present invention, the image display apparatus, comprises: an image data processing section to convert (n+m)-bit monochromatic image data represented by a single channel to a n-bit color display image-data group represented by plural channels including three channels or more, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2; and a color image display section to display a color image on it, based on the n-bit color display image-data group outputted by the image data processing section; wherein the image data processing section includes: a candidate selection section to select "H" sets of signal-values of the plural channels out of all combinations of signal-values of the plural channels included in the n-bit color display image-data group as candidate color display signal-value sets, wherein numeral "H" indicates a positive integer; a signal value decision section to determine a single color display signal-value set, to be correlated with each of signal values represented by the (n+m)-bit monochromatic image data, from among the "H" sets of candidate color display signal-value sets, with respect to each of the signal values represented by the (n+m)-bit monochromatic image data; and a correlation establishing section to establish the correlation by correlating each of the signal values represented by the (n+m)-bit monochromatic image data with the color display signal-value set determined by the signal value decision section while corresponding thereto.

(11) According to another aspect of the present invention, in the image display apparatus recited in item 10, numeral "H", being a number of the candidate color display signal-value sets, fulfills equations indicated as follows;

$$H = C \times 2^n$$

$$2^{(m+1)} \leq C \leq 2^{(m+4)}.$$

(12) According to still another aspect of the present invention, in the image display apparatus recited in item 10 or 11, the image data processing section further includes: a luminance information acquiring section to acquire luminance information corresponding to each of the signal values represented by the (n+m)-bit monochromatic image data; and a chromaticity information acquiring section to acquire chromaticity information corresponding to each of the signal values represented by the (n+m)-bit monochromatic image data; and the signal value decision section determines the single color display signal-value set, which is correlated with each of the signal values represented by the (n+m)-bit monochromatic image data, based on the luminance information and the chromaticity information, respectively acquired by the luminance information acquiring section and the chromaticity information acquiring section.

(13) According to still another aspect of the present invention, in the image display apparatus recited in item 10 or 11, the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

(14) According to yet another aspect of the present invention, in the image display apparatus recited in item 10 or 11, the image data processing section further includes: a color tone selecting section to select a desired color tone of the image, to be displayed on the color monitor, from a plurality of candidate color tones; and the candidate selection section selects the candidate color display signal-value sets, so that the desired color tone corresponds to a color tone of the color image to be displayed on the color image display section.

(15) According to an image display apparatus reflecting still another aspect of the present invention, the image display apparatus, comprises: an image data processing section to convert (n+m)-bit monochromatic image data represented by a single channel to a n-bit color display image-data group represented by plural channels including three channels or more, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2; and a color image display section to display a color image on it, based on the n-bit color display image-data group outputted by the image data processing section; wherein the image data processing section includes: a candidate selection section to select "H" sets of signal-values of the plural channels out of all combinations of signal-values of the plural channels included in the n-bit color display image-data group as candidate color display signal-value sets, wherein numeral "H" indicates a positive integer; a luminance information acquiring section to acquire luminance information corresponding to each of the signal values represented by the (n+m)-bit monochromatic image data; a signal value decision section to determine a single color display signal-value set, to be correlated with each of signal values represented by the (n+m)-bit monochromatic image data, from among the "H" sets of candidate color display signal-value sets, based on the luminance information acquired by the luminance information acquiring section, with respect to each of the signal values represented by the (n+m)-bit monochromatic image data; and a correlation establishing section to establish the correlation by correlating each of the signal values represented by the (n+m)-bit monochromatic image data with the color display signal-value set determined by the signal value decision section while corresponding thereto.

(16) According to another aspect of the present invention, in the image display apparatus recited in item 15, numeral "H", being a number of the candidate color display signal-value sets, fulfills equations indicated as follows;

$$H = C \times 2^n$$

$$2^{(m+1)} \leq C \leq 2^{(m+3)}.$$

(17) According to still another aspect of the present invention, in the image display apparatus recited in item 15 or 16, the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

(18) According to yet another aspect of the present invention, in the image display apparatus recited in item 15 or 16, the image data processing section further includes: a color tone selecting section to select a desired color tone of the image, to be displayed on the color monitor, from a plurality of candidate color tones; and wherein the candidate selection section selects the candidate color display signal-value sets, so that the desired color tone corresponds to a color tone of the color image to be displayed on the color image display section.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE PREFERRED EMBODIMENT

First Embodiment

Figure 1:
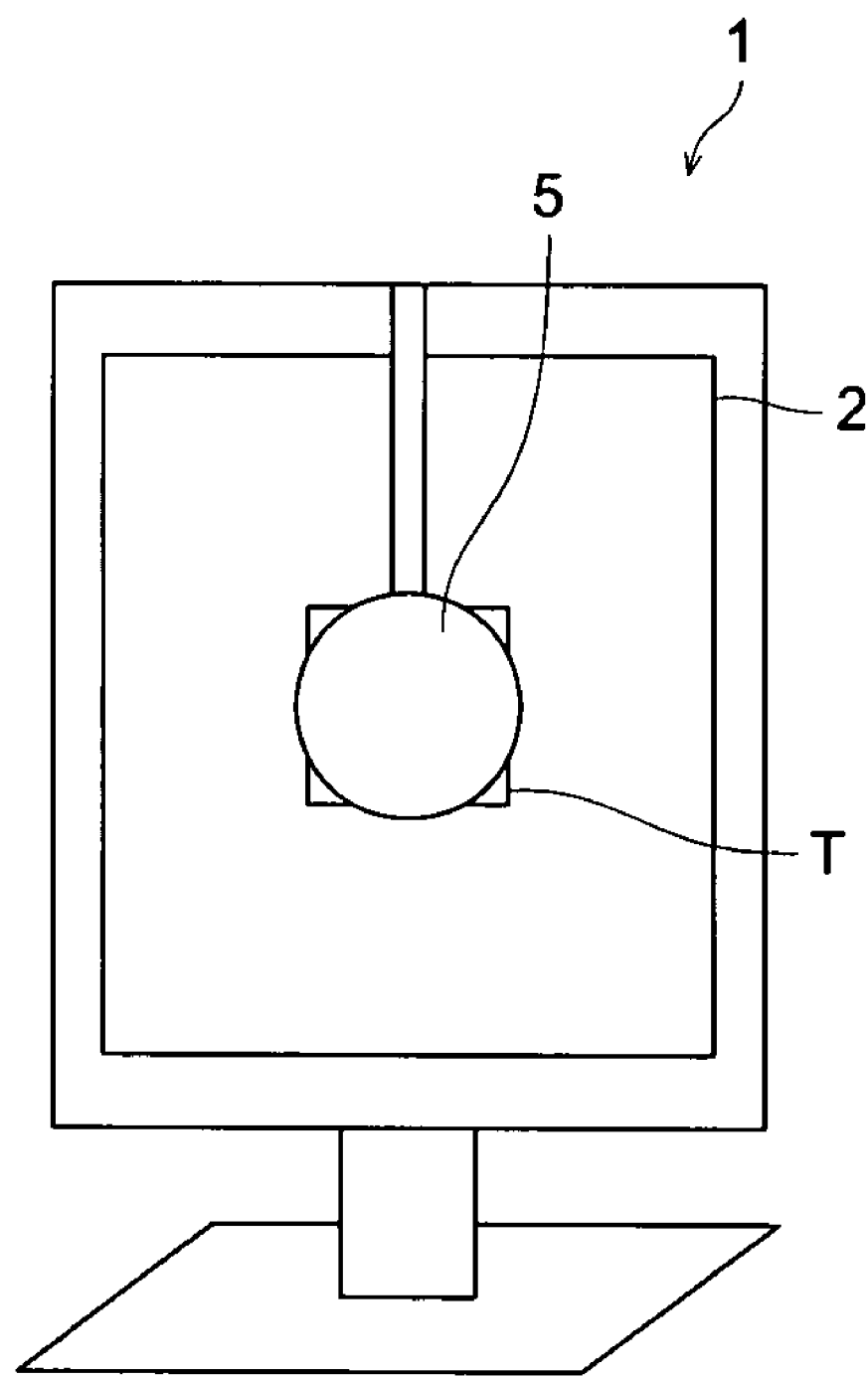
FIG. 1 is a front view of a color image displaying section of an image display apparatus embodied in the present invention.

Referring to the drawings, the first embodiment of the image display embodied in the present invention will be detailed in the following. However, the scope of the present invention is not limited to the illustrations.

Figure 2:
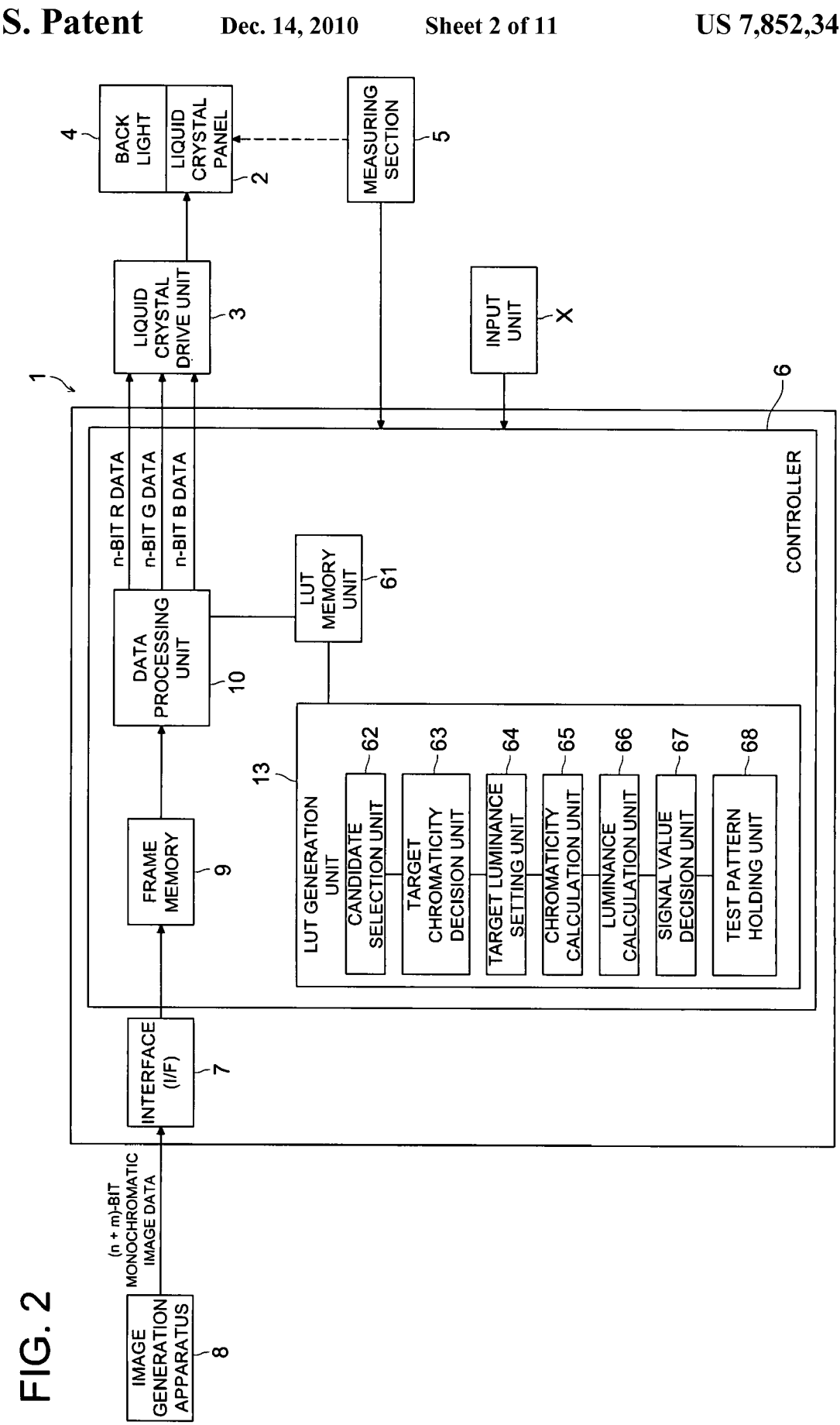
FIG. 2 is a block diagram indicating a brief configuration of an image display apparatus embodied in the present invention as the first embodiment.

FIG. 1 is a front view of a color image displaying section of an image display apparatus 1 embodied in the present invention. Further, FIG. 2 is a block diagram indicating a brief configuration of the image display apparatus 1 embodied in the present invention as the first embodiment. The image display apparatus 1, for example, is a color monitor for a medical diagnostic apparatus. As shown in FIG. 2, the image display apparatus 1 includes a liquid crystal panel (LCD, liquid crystal display) 2 as a color image displaying section for displaying a color image on the basis of an internal signal value and a liquid crystal drive section 3 as a display drive section for driving the color image displaying section.

The kind of the liquid crystal panel 2 applicable to this embodiment is not restricted particularly and with respect to the method for the liquid crystal drive section 3 to drive the liquid crystal panel 2, various drive methods such as the TN (twisted nematic) method, STN (super twisted nematic) method, MVA (multi-domain vertical alignment) method, and IPS (in-plane switching) method can be applied. Further, in this embodiment, the liquid crystal panel 2, by a color filter not drawn, can reproduce the 8-bit (256 grades) grayscale respectively for red (R), green (G), and blue (B).

Further, in this embodiment, a liquid crystal panel composed of three colors of red (R), green (G), and blue (B) is used, though the embodiment is not limited to the three colors of red (R), green (G), and blue (B) and for example, three colors of yellow (Y), magenta (M), and cyan (C) are acceptable. Further, four or more colors are acceptable and six colors of R, G, B, Y, M, and C or six colors of red (R1, R2), green (G1, G2), and blue (B1, B2), which are different in color tone, are acceptable. The image process which will be described later is neither limited to three colors of red (R), green (G), and blue (B). Further, this embodiment can be applied to an image display apparatus for not only multi-color displaying by a color filter, but also multi-color displaying by switching light sources of a plurality of colors.

Further, the image display apparatus 1 has a back light 4 for irradiating light to the liquid crystal panel 2 from the non-observation side. With respect to the back light 4, if it provides light sufficiently enough to illuminate the liquid crystal panel 2, for example, an LED, a cold cathode fluorescent tube, a hot cathode fluorescent tube, and other light emitting elements can be applied, though it is preferable to display an image at a maximum luminance of 500 to 5000 cd/m², so as to suitably apply it to a medical monitor.

Further, the image display apparatus 1 has a measuring section 5 for measuring a display characteristic of an image displayed in a specific target area T of the liquid crystal panel 2. For the measuring section 5, a known sensor such as a luminance meter of a chromaticity meter can be used in accordance with the kind of the liquid crystal panel 2. Further, although the measuring section 5 shown in FIG. 1 is a contact type sensor, it is needless to say that any kinds of measuring devices including a noncontact type sensor can be applicable for this purpose. Still further, it is also applicable that the measuring section 5 is configured into the apparatus either internally or externally. The measuring section 5 is connected to an LUT generation section 13 which will be described later and the LUT generation section 13 measures the display characteristic displayed every switching of a test pattern displayed on the liquid crystal panel 2 and the measured results are outputted to the LUT generation section 13.

The display characteristic of the liquid crystal panel 2 is information on the R, G, and B values inputted to the liquid crystal panel 2 and the luminance and/or chromaticity of the display light for them. For the information on the luminance and/or chromaticity, indexes of the color specification used generally can be used. For example, various kinds of color specification systems, which are defined by the CIE, such as the XYZ color specification system, the $X_{10}Y_{10}Z_{10}$ color specification system, the xyz chromaticity coordinates, the $x_{10}y_{10}z_{10}$ chromaticity coordinates, and, as the USC diagrams (Uniform Chromaticity Scale diagram), the L*a*b* color specification system, the L*C*h* color specification system, the L*u*v* color specification system, etc., may be cited, though the scope of the present invention is not limited to them.

The information on the luminance and/or chromaticity may be measured at predetermined timing using the measuring section 5 by displaying the test pattern in the target area T of the liquid crystal panel 2 or may store results obtained by displaying and measuring the test pattern on the liquid crystal panel 2 at time of shipment from the factory. Further, without using measured results for each display apparatus, the correlation of the information on the luminance and/or chromaticity to the R, G, and B values may be stored as a predetermined conversion formula.

The position and magnitude of the specific target area T where the measuring section 5 measures the display characteristic are not restricted particularly, though in this embodiment, the region of an area of about 10% in the central part of the display screen of the liquid crystal panel 2 is designated. The measuring section 5 is connected online to the image display apparatus 1, though for example, it is possible to measure the display characteristic using a measuring section not connected online to the image display apparatus 1 and input the measured results to the image display apparatus 1 via an input section such as a keyboard.

Further, in the image display apparatus 1, for example, a controller 6 for controlling the liquid crystal drive section 3 composed of a CPU (Central Processing Unit), a ROM (Read Only Memory) for storing various control programs, and a RAM (Random Access Memory) for temporarily storing image data (these sections are not drawn), an interface (I/F) 7 for connecting the controller 6 to an external apparatus, and an input section 15 are installed.

To the interface 7, an image generation apparatus 8 as an external apparatus is connected. The image generation apparatus 8 supplies, for example, monochromatic image data 12 bits long, thus to the interface 7, an input signal value of the monochromatic image data (hereinafter, also referred to as "value") is inputted. The scope of the image generation apparatus 8 is not restricted particularly, while, for example, various kinds of medical diagnostic apparatuses, such as an X-ray diagnostic apparatus, an MRI (magnetic resonance imaging) diagnostic apparatus, various CT (computed tomography) apparatuses, etc., can be cited as the image generation apparatus 8.

In the controller 6, a frame memory (FM shown in FIG. 2) 9, a data processing section 10, an LUT memory section 61, and the LUT generation section 13 are installed.

The frame memory 9 stores the monochromatic image data for every frame, inputted from the image generation apparatus 8 through the interface 7.

The data processing section 10 data-distributes 1-channel (n+m)-bit monochromatic image data inputted from the frame memory 9 to three channels of R, G, and B and converts it to n-bit R, G, and B display image data. Here, in this embodiment, the data processing section 10 of the controller 6 converts monochromatic image data (n+m) (n indicates a positive integer of 8 or more and m indicates a positive integer of 2 or more) bits long to R, G, and B display image data n bits long on the basis of a preset correlation. Concretely speaking, the data processing section 10 converts the inputted (n+m)-bit monochromatic image data to the n-bit R, G, and B image data by data-distributing the inputted (n+m)-bit monochromatic image data into the R, G, and B signal values based on the LUT serving as the correlation stored in advance in the LUT memory section 61. Namely, in this embodiment, the configuration constituted by the measuring section 5, the controller 6, and the input section 15 serve as an image data processing section embodied in the present invention.

In this embodiment, the liquid crystal panel 2 displays an image in three colors of R, G, and B, so that the monochromatic image data is converted to R, G, and B display image data as color display image data of three channels of R, G, and B, though when displaying an image in four or more colors by the display apparatus, it is desirable to convert it to image data of the number of channels in correspondence to the number of colors displayed.

The LUT generation section 13 includes a candidate selection section 62, a target chromaticity decision section 63, a target luminance decision section 64, a chromaticity calculation section 65, a luminance calculation section 66, a signal value decision section 67, and a test pattern holding section 68 and functions as a correlation establishing section for generating an LUT as a correlation on the basis of the display characteristic of the liquid crystal panel 2. The LUT generation section 13 is connected to the LUT memory section 61, which stores an LUT generated by the LUT generation section 13. Here, the LUT generation section 13, at time of shipment of the image display apparatus 1 from the factory or every lapse of a specified period of time, measures the display characteristic of the liquid crystal panel 2 which will be described later and generates an LUT.

The target chromaticity decision section 63 decides a target chromaticity corresponding to each signal value of the monochromatic image data and the target luminance setting section 64 decides a target luminance corresponding to each signal value of the monochromatic image data.

The test pattern holding section 68 holds a plurality of solid image data (R, G, and B values) displayed as a test pattern on the liquid crystal panel 2. The number and kinds of test patterns to be stored are not restricted particularly, and when all combinations of R, G, and B values are used as a test pattern, an precise display characteristic can be preferably measured, though all the combinations of R, G, and B values include about 16.77 millions ($=256^3$) colors, so that it is difficult to realize it. Therefore, it is preferable to restrict beforehand combinations of R, G, and B values under a predetermined condition.

In this embodiment, 256 colors in which the R, G, and B values are equivalent are used as a test pattern. Further, to improve the accuracy of measurement, it is possible to display and measure a combination in which at least one of the equivalent R, G, and B values is increased or decreased within a predetermined range as a test pattern.

The LUT generation section 13 measures color stimulus values X, Y, and Z when a test pattern is displayed by the measuring section 5 and inputs measured results. Here, the value indicated by Y among the color stimulus values indicates luminance.

The chromaticity calculation section 65 calculates chromaticity for each of the candidate R, G, and B display image data selected by the candidate selection section 62 and the luminance calculation section 66 calculates luminance for each of the candidate R, G, and B display image data selected by the candidate selection section 62. In this connection, the term of "candidate R, G, and B display image data" (hereinafter, also referred to as candidate color display-signal value sets, or candidate colors, for simplicity) indicates a data group of combinations of R, G, and B signal values, selected from all of the displayable combinations represented by the color display image data and cited as the candidate colors, since the candidate R, G, and B display image data have possibility to be selected, when correlating the R, G, and B signal values to each of the P values represented by the input signal value of the monochromatic image data.

The chromaticity calculation section 65 and luminance calculation section 66, on the basis of the color stimulus values of the test pattern measured by the measuring section 5 and the R, G, and B values, generate an RGB-XYZ estimation formula for approximately estimating color stimulus values X, Y, and Z when R, G, and B image data of combination of unmeasured R, G, and B values are displayed on the liquid crystal panel 2. The RGB-XYZ estimation formula is expressed by an equation (1) indicated as follow.

$$\begin{pmatrix} (X - X\min)/(X\max - X\min) \\ (Y - Y\min)/(Y\max - Y\min) \\ (Z - Z\min)/(Z\max - Z\min) \end{pmatrix} = \begin{pmatrix} C_{XR} & C_{XG} & C_{XB} \\ C_{YR} & C_{YG} & C_{YB} \\ C_{ZR} & C_{ZG} & C_{ZB} \end{pmatrix} \begin{pmatrix} (R/255)^\gamma \\ (G/255)^\gamma \\ (B/255)^\gamma \end{pmatrix} \quad (1)$$

The method for generating the equation (1) is not restricted particularly, though for example, a method, in the general Formula (1), for obtaining γ and 10 unknown variables of $C_{XR}$, $C_{XG}$, - - - by the method of least squares can be applied. Further, there is an advantage available that as the number of test patterns to be displayed is increased, an accurate RGB-XYZ estimation formula can be generated. On the other hand, there is an advantage available that as the number of test patterns to be displayed is decreased, an RGB-XYZ estimation formula can be generated in a short time.

The chromaticity calculation section 65 and luminance calculation section 66, on the basis of the equation (1) indicated above, calculate chromaticity information and luminance information respectively corresponding to the candidate R, G, and B display image data.

The candidate selection section 62 selects $C \times 2^n$ ($2^{(m+1)} \leq C \leq 2^{(m+4)}$) sets of R, G, and B signal values out of all combinations ($256^3$ sets) of R, G, and B signal values represented by a 8-bit/RGB color display image data group as the candidate R, G, and B display image data (namely, the candidate color display-signal value sets, or the candidate colors, for simplicity).

In this connection, the general expression of the 8-bit/RGB color display image data group is an "n-bit/f-channel color display image data group" (n: integer equal to or more than eight), which is represented by plural channels (f-channel) equal to or more than three channels. Accordingly, a general expression of the above is such that the candidate selection section 62 selects H=C×$2^n$ ($2^{(m+1)} \leq C \leq 2^{(m+4)}$) sets of values out of all combinations (($2^n)^f$ sets) of f-channel signal values represented by the n-bit/f-channel color display image data group as the candidate f-channel display image data (namely, the candidate color display-signal value sets, or the candidate colors, for simplicity).

Figure 3:
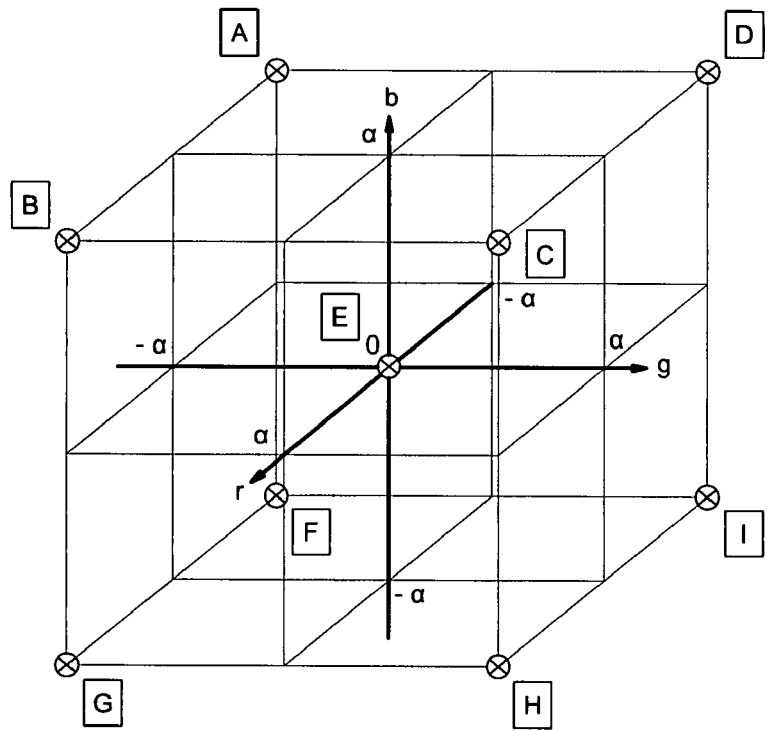
FIG. 3 is an explanatory view indicating a range of candidate colors in the first embodiment.

Concretely speaking, the candidate selection section 62 selects reference colors provisionally determined as the target gradation characteristic and near colors. In the method for selecting the near colors, for instance, the candidate colors are selected within a range added with an offset value of ±α (α: natural number) of each of the R, G, and B signal values with respect to the each of the reference colors (refer to FIG. 3). In this connection, if each of the R, G, and B signal values resides outside the displayable range (when the signal value is smaller than zero, or is equal to or greater than $2^n$) as a result of the offset adding operation, such the R, G, and B signal values are excluded from the candidate colors. Further, if some candidate colors are duplicated with each other as a result of the offset adding operation, the number of duplicated candidate colors is excluded from the counted number of selected candidate colors. For instance, when α=2, since it is possible for each of the R, G, and B signal values to take five ways of numerical value in a range of −2 to +2, 125 (=5×5×5) sets of candidate colors can be generated with respect to one reference color. In order to prevent the duplication of candidate colors of adjacent reference colors, it is preferable to further reduce the offset number to a lower number from the abovementioned 125 sets.

Now, the R, G, and B signal values of the reference color are expressed by an equation (2) indicated as follow.

$$\begin{cases} R = s \\ G = s \\ B = s \end{cases} \quad s = 0 \text{ to } 2^n - 1 \text{ for } n\text{-bit image display apparatus} \quad (2)$$

The scope of the R, G, and B signal values of the reference color is not limited to equivalent signal values. For instance, in the case of the bluish tone color, the R, G, and B signal values of the reference color are expressed by an equation (3) indicated as follow.

$$\begin{cases} R = Int(\beta r \times s) \\ G = Int(\beta g \times s) \\ B = s \end{cases} \quad \begin{array}{l} \text{where: } 0 < \beta r < 1 \\ 0 < \beta g < 1 \\ s = 0 \text{ to } 2^n - 1 \text{ for } n\text{-bit} \\ \text{image display apparatus} \end{array} \quad (3)$$

Further, the candidate selection section 62 determines the value of α, considering a balance between the display gradation number and the chromaticity. Although the value of α is merely defined as a positive integer in the present embodiment, it is preferable that the value of α is equal to or smaller than three, so as not to excessively increase the number H of candidate colors. On the other hand, if the value of α is equal to or greater than four, the selection range for selecting the candidate colors is excessively widened. As a result, there arises a fear that the arithmetic calculation time period would be excessively extended, and at the same time, the color display image data having an undesired chromaticity would be selected.

Further, the candidate selection section 62 determines the reference colors, which are to be employed for selecting the candidate colors corresponding to the color tone to be selected on the basis of the user's taste. For instance, it is applicable that the candidate selection section 62 stores in advance the data of either the reference colors or the candidate colors derived in advance by employing the equation (2) or the equation (3), corresponding to each of various color tones. In other words, the candidate selection section 62 also serves as a color tone selecting section for selecting a specific color tone desired by the user, from a plurality of candidate color tones, for the image to be displayed on the color image display section.

The candidate selection section 62 selects the R, G, and B display image data, residing in ranges of ±α from the reference colors and within a monochrome area, as the candidate colors. Hereinafter, the monochrome area is defined as follows. With respect to the color tone when viewing various kinds of monochromatic film images of a blue tone base by employing a viewing box with backlight, when actual measurements of the chromaticity in each density of each film and each light source are concentrated within a considerably narrow range. Further, considering errors possibly included in the actual measurements of the chromaticity, etc., it is preferable that each of x and y has an allowance in a range of about 0.01-0.02. As a result, in the present embodiment, the monochrome area is defined as an area surrounded by the lines connecting the coordinate points of (0.2, 0.275), (0.275, 0.225), (0.325, 0.4), (0.4, 0.35) on the CIE chromaticity coordinates.

When the tristimulus values Y of display color of the RGB color display image data, coordinate point (x, y) on the CIE chromaticity coordinates, target values of x0, y0 on a predetermined chromaticity coordinates, color difference $\Delta xy = \{(x-x0)^2 + (y-y0)^2\}^{1/2}$, and allowance of predetermined color difference $\Delta xy0$ are established, it is preferable that the candidate selection section 62 selects only such RGB color display image data that fulfills the relationship of $\Delta xy \leq \Delta xy0$, as the candidate colors.

For instance, the candidate selection section 62 determines target values x0, y0 as the chromaticity coordinates (x, y) in case of (R, G, B)=(255, 255, 255), and sets the allowance of predetermined color difference $\Delta xy0$ at 0.01, so as to establish the RGB color display image data, which fulfills the relationship of $\Delta xy \leq \Delta xy0$, as the candidate color.

In this connection, since it is possible to fiderally reproduce a color tone of a conventional blue-base film image, it is preferable that both target values x0, y0 are established in such a manner that both of them decreases in at least a part of the luminance range. Concretely speaking, this can be realized by making the values of βr, βg in the equation (3) as small as possible in at least a part of the luminance range. The smaller the luminance at the time of displaying, namely, the target luminance Y corresponding to each of P values in at least a part of the luminance range is, the smaller the values of βr, βg become.

The number of candidate colors selected by the candidate selection section 62, namely, $H = C \times 2^n$ is determined on the basis of the compromise between a degree of shortening an arithmetic calculating time and a number required for multi-gradation displaying operation. Generally speaking, with respect to the display of the monochromatic image, it is unnecessary to take all the colors of 16.00 millions as the objects of the candidate colors. Taking such the large number of colors merely extends the arithmetic calculating time.

In this connection, it is applicable that the candidate selection section 62 selects a candidate color in respect to each of P values of the monochromatic image data at every time when conducting the candidate color selecting process detailed later. Further, it is also applicable that the candidate selection section 62 selects candidate colors in advance and stores the selected candidate colors in the apparatus, instead of employing the aforementioned method in which the offset is added to the reference value so as to automatically select the candidate colors.

The signal value decision section 67 determines R, G and B values of the RGB color display image data corresponding to each of P values of the monochromatic image data. Concretely speaking, the signal value decision section 67 determines a single selected color from the candidate RGB color display image data, based on the chromaticity information outputted from the target luminance setting section 64 and the luminance calculation section 66, and establishes the R, G and B values of the selected color as the RGB color display image data, while correlating them with each of P values of the monochromatic image data.

Next, the image display method embodied in the present invention will be detailed in the following.

At first, the LUT generation process executed by the LUT generation section 13 will be explained in detail. The LUT generation process is a process of generating or correcting an LUT so as to display a monochromatic image of an appropriate color tone by the image display apparatus 1 and for example, at time of shipment of the image display apparatus 1, the process is started by the operation of the input section 15.

Figure 4:
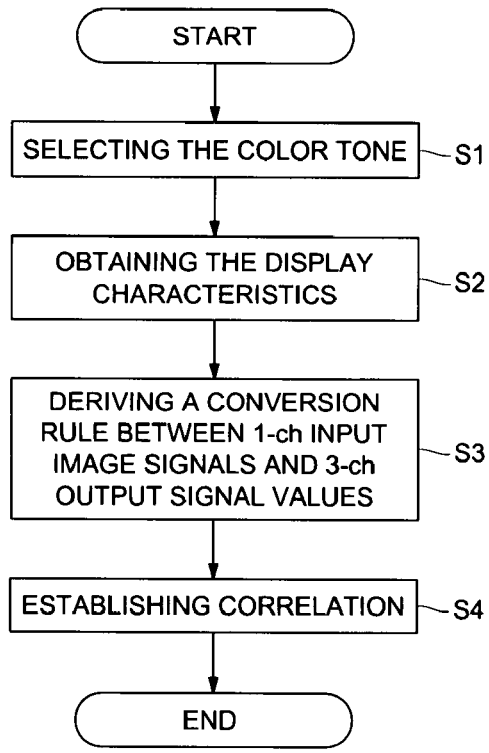
FIG. 4 is a flowchart showing a conversion rule generating process in the first embodiment.

In the LUT generation process, a conversion rule generation process as a correlation establishing process in this embodiment is executed (refer to FIG. 4). The conversion rule generation process is broadly divided into a process of selecting the color tone of a display image desired by a user (Step S1), a process of obtaining the display characteristic of the liquid crystal panel 2 (Step S2), a process of deriving a conversion rule (Step S3), and a correlation setting process (Step S4).

Figure 5:
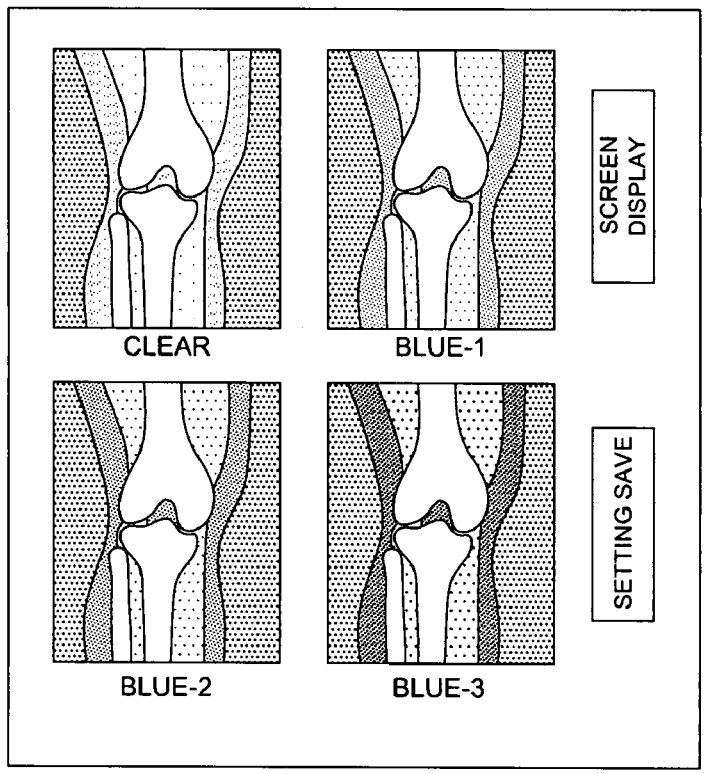
FIG. 5 is an explanatory view indicating screens to be displayed in a color tone selecting process in the first embodiment.

In the color tone selection process (Step S1), for example, a plurality of screens of different color tones as shown in FIG. 5 are displayed on the liquid crystal panel 2, and a desired display image color tone is selected by a user using the input section X (refer to FIG. 2) such as a mouse, and the information is stored. In FIG. 5, four kinds of X-ray transmitted images in total including the color tone of neutral gray and three kinds of bluish color tones different in depth are shown, and the process is structured so as to click the mouse pointer on the image of the color tone desired by the user, thereby select the color tone, though the color tone selection method is not limited to it. Based on the result of the color tone selecting operation conducted in the color tone selection process, the candidate selection section 62 establishes the reference color by employing the correlation determined by conducting the low gradation correlation processing. For instance, the reference color corresponding to the user's desire is determined by employing the equation (2) or the equation (3). Further, it is also applicable that the candidate selection section 62 selects the reference color corresponding to the color tone desired by the user from the plurality of reference colors stored in advance to determine it.

In the display characteristic acquisition process (Step S2), the correspondence of the R, G, and B values inputted to the liquid crystal panel 2 to the information on the luminance and/or chromaticity of the display light from the liquid crystal panel 2 is obtained. More in detail, in the display characteristic acquisition process (Step S3), the image display apparatus 1 measures the display characteristic of the liquid crystal panel 2 by the LUT generation section 13. Namely, the LUT generation section 13 makes the liquid crystal panel 2 display sequentially the test patterns held by the test pattern holding section 68 and makes the measuring section 5 measure the color stimulus values X, Y, and Z of the CIE XYZ color specification system every display switching of the test pattern.

The chromaticity calculation section 65 and luminance calculation section 66, on the basis of the R, G, and B values of the test pattern and the measured color stimulus values X, Y, and Z, generate the RGB-XYZ estimation formula expressed by the equation (1). Here, the LUT generation section 13, to generate a more accurate RGB-XYZ estimation formula, may display the color in which the R, G, and B values of the test pattern are increased or decreased within a predetermined range as a test pattern and measure the color stimulus values of the liquid crystal panel 2. The increasing and decreasing range of the R, G, and B values of the test pattern is not restricted particularly, though to prepare a more accurate estimation formula, the concerned range preferably coincides with the range of candidate colors.

The conversion rule derivation process (Step S3), on the basis of the correspondence of the information on the luminance and/or chromaticity to the R, G, and B values of the test pattern, derives an LUT as a conversion rule for converting a 1-channel monochromatic image signal value (m+n bits) to 3-channel R, G, and B values (m bits). In other words, the signal value decision section 67 serves as a signal value determining section in the conversion rule derivation process (Step S3). Further, in this embodiment, an LUT is generated as a conversion rule, though a conversion formula is acceptable. Further, one conversion formula or one LUT is acceptable and a combination of multi-grade conversion rules is acceptable.

The correlation setting process (Step S4) makes the LUT memory section 61 store the aforementioned conversion rule derived by the conversion rule derivation process (Step S3) as a correlation. Namely, in the correlation setting process (Step S4), the LUT generation section 13 functions as a correlation setting section.

Figure 6:
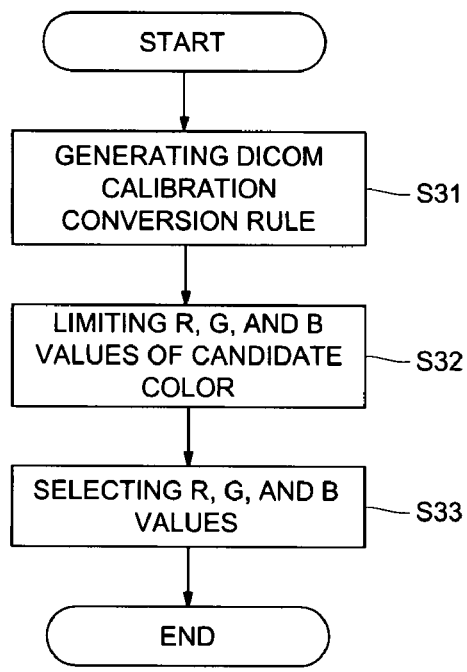
FIG. 6 is a flowchart showing a conversion rule deriving process in the first embodiment.

Here, the conversion rule derivation process (Step S3) will be explained in detail by referring to FIG. 6. In this connection, hereinafter in the present embodiment, 1-channel intermediate data serving as "internal signal values" are defined, which is to be used at the time when deriving the conversion rule aforementioned. Concretely speaking, initially, (1) a "DICOM (Digital Imaging and Communication in Medicine) calibration LUT (Look Up Table)" for correlating (n+m)-bit/1-channel monochromatic image data (P values, 1-channel signal values) with the internal signal values (1-channel signal values) and (2) a "Monochromatic Multi-Gradation LUT" for correlating the internal signal values (1-channel signal values) with the R, G and B values (3-channel signal values) are generated respectively, and then, the "DICOM calibration LUT" and the "Monochromatic Multi-Gradation LUT" are synthesized with each other, so as to make the P values correlate with the R, G and B values.

In the present embodiment, although the internal signal values is so constituted that a gradation number M of the internal signal values is set at $M=2^{12}$ (=4096), it is also applicable that the gradation number M is set at such a value as at least $M=2^{10}$, in order to achieve the multi-gradation expression, the gradation number M of which is greater than the driving gradation number of the liquid crystal panel 2 by 2 bits (4 times).

At first, the LUT generation section 13, on the basis of the display characteristic of the liquid crystal panel 2, generates DICOM calibration conversion rule for relating the internal signal value to the P value (Step S31). Here, the DICOM calibration conversion rule is preferably generated as an LUT. Further, the display luminance to the P value is preferably generated so as to correspond to the GSDF (Grayscale Standard Display Function) specified in DICOM PS 3.14 and by the DICOM calibration which is conventionally known, the display luminance to the P value may be generated using the grayscale standard display function.

Figure 7:
FIG. 7 shows explanatory tables indicating a relationship between test patterns and displaying characteristic in the first embodiment.
Figure 8:
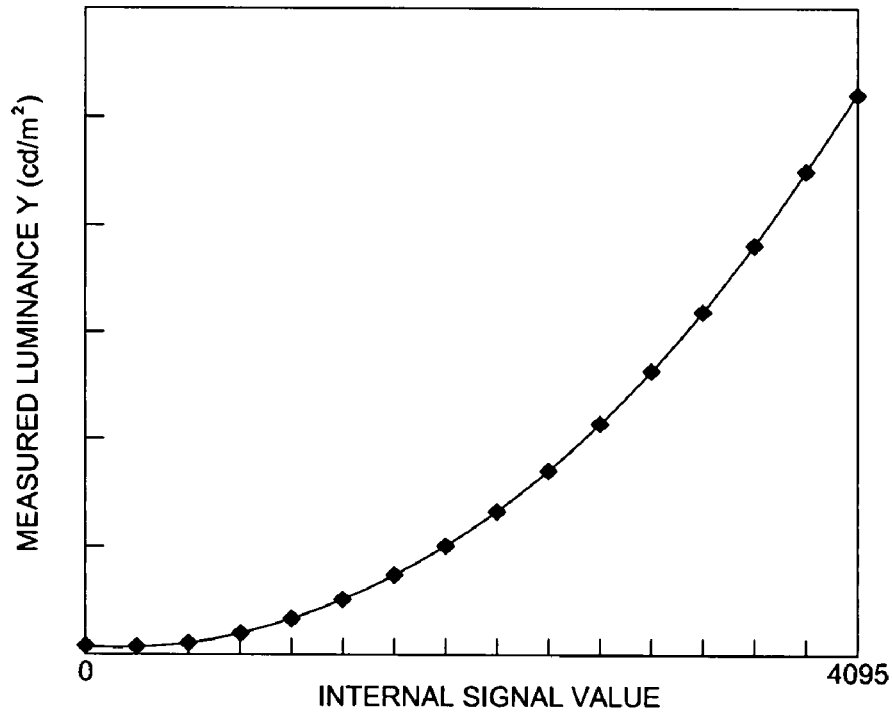
FIG. 8 shows an explanatory graph for explaining a generation of a standard display function in the first embodiment.
Figure 9:
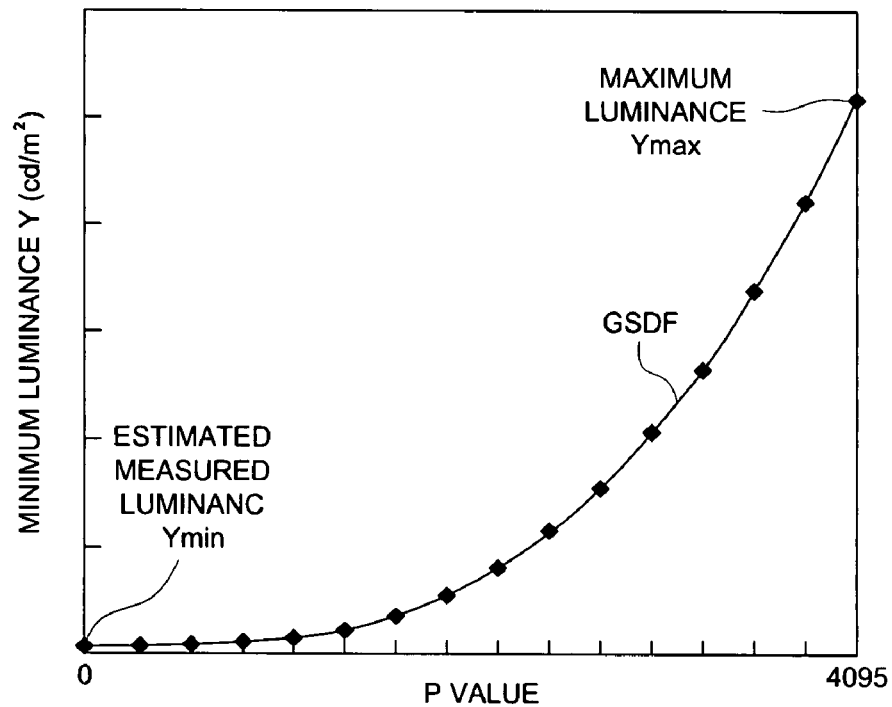
FIG. 9 shows an explanatory graph for explaining a generation of a standard display function in the first embodiment.

The measured results by the measuring section 5 are outputted to the controller 6 and the LUT generation section 13 brings the R, G, and B values into correspondence to the luminance of the test pattern. In this case, the LUT generation section 13, as shown in Table A in FIG. 7, to the internal signal values of 16 grades at 273 intervals among the internal signal values (0 to 4095) of 4096 grayscales, allocates the R, G, and B values of 16 grades at 17 intervals among the test pattern signal values R, G, and B of 256 grayscales, and brings the measured luminance at the respective R, G, and B values into correspondence to them. And, the LUT generation section 13 brings the respective internal signal values into correspondence to the R, G, and B values by proportional allotment. In this case, the R, G, and B values may not always be integers. Furthermore, when the estimated measured luminance corresponding to the R, G, and B values is calculated, for example, using the equation (1) aforementioned, the estimated measured luminance (refer to Table B and FIG. 8) for the internal signal values of 4096 grayscales are estimated. Then, the LUT generation section 13 obtains the lowest luminance and highest luminance of the estimated measured luminance and allocates the maximum luminance to the lowest luminance to the P values of 4096 grayscales on the basis of the GSDF (refer to FIG. 9).

Figure 10A:
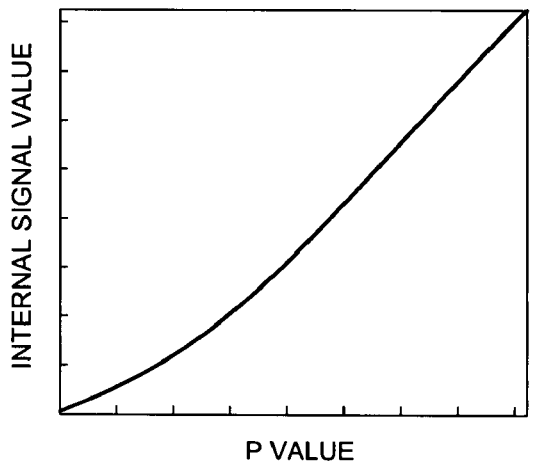
FIG. 10(a), FIG. 10(b) and FIG. 10(c), show explanatory graphs for explaining a generation of a standard display function in the first embodiment.
Figure 10B:
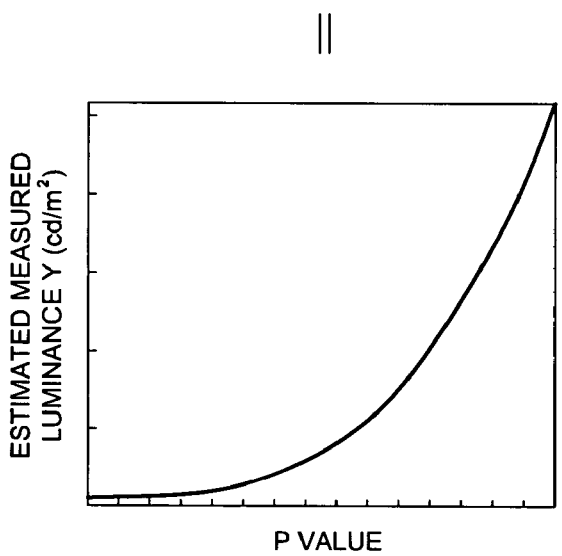
Figure 10C:
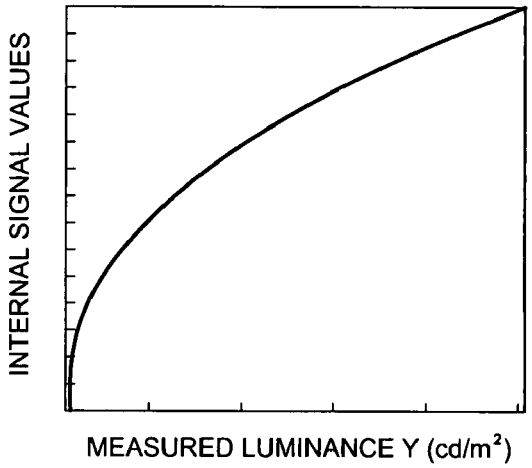

Then, as shown in FIG. 10, a calibration LUT for relating the internal signal values to the P values is generated. When the image display apparatus 1 is adjusted to the characteristic of the GSDF curve, the internal signal values and P values are equivalent and the generated calibration LUT is a proportional straight line at a slope of 1. On the other hand, when the image display apparatus 1 is not adjusted, the calibration LUT is a curved line in accordance with the characteristic of the liquid crystal panel 2.

In the candidate selection process, with respect to each of the internal signal values of the monochromatic image data, the candidate selection section 62 selects $C \times 2^n$ ($2^{(m+1)} \leq C \leq 2^{(m+4)}$) sets of R, G, and B signal values of the candidate R, G, and B display image data (candidate colors) from $256^3$ sets of R, G, and B signal values of the RGB color display image data (Step S32). By limiting the candidate colors within the monochromatic range, it preferably becomes possible not only to shorten the arithmetic calculation time for the following process, but also to exclude the RGB color display image data outside the monochromatic range from the selection.

The signal value determining process, from among the selected candidate colors, selects R, G and B values based on the luminance (Step S33). The R, G and B values based on the luminance are selected in this way, thus the color tone of the image and the number of grayscales can be made compatible with each other.

Figure 11:
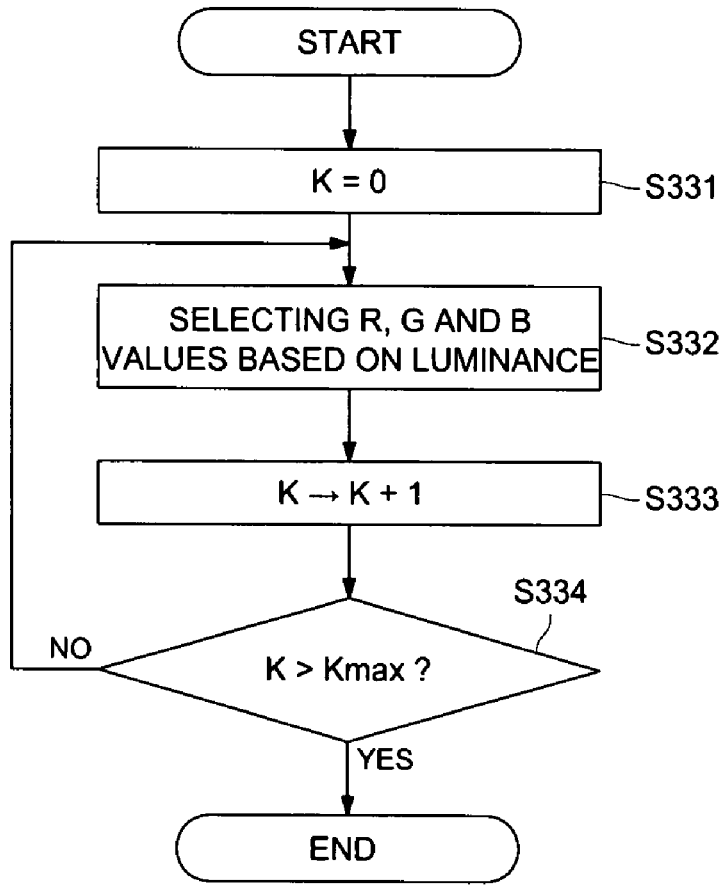
FIG. 11 shows a flowchart indicating a selecting process of R, G and B signal values in the first embodiment.

Here, the selection of the R, G, B values in the signal value determining process will be explained by referring to FIG. 11.

At first, assuming k=0 (Step S331), a target luminance Y (k) for the internal signal value k is decided by the target luminance setting section 64. Here, the target luminance Y (k) is referred to as luminance of an image, which will be represented on the liquid crystal panel 2, when the P value, which will be the internal signal value k, is inputted to the image display apparatus 1. Concretely speaking, the estimated measured luminance shown in Table B can be used as a target luminance Y (k).

Figure 12:
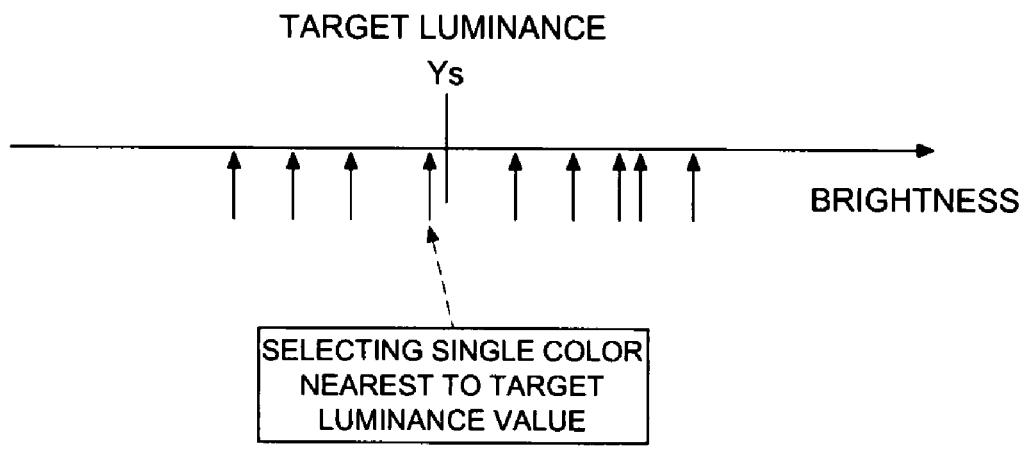
FIG. 12 shows an explanatory view indicating a selecting operation of a selected color based on chromaticity in the first embodiment.

Then, the luminance calculation section 66 calculates luminance Y of each candidate color using the equation (1) aforementioned (the luminance calculation process). Successively, as shown in FIG. 12, the signal value decision section 67 selects a specific candidate color nearest to the target luminance Y (k) as the selected color.

The LUT generation section 13 takes the R, G, and B values of the color selected in this way as R, G, and B values corresponding to the internal signal value k. Successively, the LUT generation section 13, also for the internal signal value (k+1), selects similarly the R, G, and B values (Step S333, NO at Step S334), selects the R, G, and B values for all the internal signal values of 4096 grayscales, and finishes the generation of the LUT (YES at Step S334).

Figure 13:
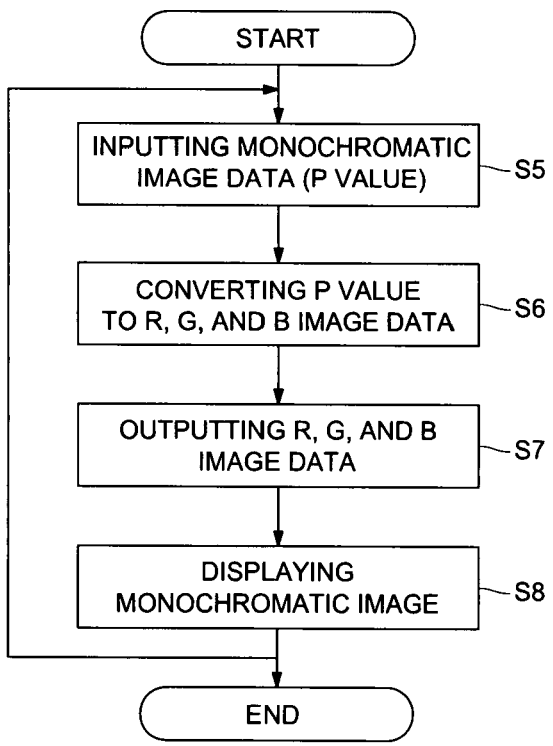
FIG. 13 shows a flowchart indicating an image display method in the first embodiment.

Next, the image display method to be conducted by the image display apparatus 1 will be explained by referring to FIG. 13.

Firstly, 12-bit monochromatic image data is inputted to the image display apparatus 1 from the image generation apparatus 8 (Step S5). The input monochromatic image data is inputted to the controller 6 via the interface 7. The monochromatic image data inputted to the controller 6 are stored in the frame memory 9.

The monochromatic image data stored in the frame memory 9 is outputted sequentially to the data processing section 10. Initially, the data processing section 10 converts the monochromatic image data to the internal signal values of 4096 gradations, and then, data-distributes the internal signal values into the R, G, and B values based on the LUT stored in advance in the LUT memory section 61, so as to converts them to 8-bit R, G, and B image data (Step S6).

At Step S6, the data processing section 10 performs the "DICOM calibration LUT process" for the P value, thereby converts it to the internal signal value k, and then performs the "Monochromatic Multi-Gradation LUT" process for converting the internal signal value k to the R, G, and B values. Here, the LUT process does not need to be composed of 2 grades and for example, an LUT composed of a calibration LUT and a conversion LUT from an internal signal value to R, G, and B values is prepared and one process using the composite LUT may be used as an LUT process.

The R, G, and B image data converted at Step S6 is outputted to the liquid crystal drive section 3 (Step S7) and the liquid crystal drive section 3 displays an image based on the R, G, and B image data and realizes a 10-bit monochromatic image (Step S8). Further, this embodiment is explained by the process free of frame division display, though the frame division display is also available. In the case of frame division display, the R, G, and B image data converted at Step S6 is divided into four frame data, and the respective frame data is stored in a second frame memory not drawn, and the stored frame data is outputted to the liquid crystal drive section 3 by switching sequentially. By doing this, it becomes possible to display a monochromatic image represented by the image data having a bit length exceeding that of 12 bits.

As described in the foregoing, according to the image display apparatus 1 embodied in the present invention, since the characteristics of the liquid crystal panel 2 are measured in order to generate or correct the LUT concerned, it becomes possible to precisely reproduce the monochromatic image without being influenced by variations in the display characteristics of the liquid crystal panel 2.

Further, since only the candidate colors, which is included in a range of ±α from the reference color and chromaticity of which resides within the monochromatic area, are selected, there is no fear that the RGB display image data residing outside the monochromatic range are selected. In addition to the above, since the signal value determining process can be conducted by calculating the luminance with respect to such the RGB display image data, it also becomes possible to minimize the length of the arithmetic calculation time interval. Still further, by limiting the selected color within the monochromatic area, even if a single selected color is selected in the signal value determining process by employing a simple algorism, it becomes possible to securely establish the selected color within the monochromatic area.

Still further, since the R, G, and B values of the candidate colors are offset in a range of ±α without limiting them to the equivalent values, it becomes possible not only to increase choice as the candidate colors, but also to achieve the multi-gradation display having the gradation characteristics exceeding that of the image display section. Accordingly, it also becomes possible to make the image display section display an image having a high gradation resolution capability.

Still further, since the RGB-XYZ estimation formula can be employed for estimating the luminance and the chromaticity, it becomes possible not only to estimate the target luminance from the internal signal values, but also to estimate the chromaticity to be displayed on the liquid crystal panel 2 from the R, G, and B values. In addition, since the luminance in respect to a plurality of candidate colors are calculated by employing the estimation formula so as to extract a single selected color, it is unnecessary to estimate the luminance of all candidate colors, and accordingly, it becomes possible not only to shorten the time interval required for the correcting operation of the LUT, but also to simplify the correcting operation of the LUT, itself.

Still further, although the controller 6 is incorporated into the image display apparatus 1 in the present embodiment, it is also applicable that another apparatus, such as a personal computer, etc., serves as the controller 6.

Yet further, although the multi-gradation display can be achieved without employing the FRC displaying mode in the present embodiment, by combining the FRC displaying mode with the present invention, a further advanced multi-gradation display could be achieved.

Second Embodiment

Figure 14:
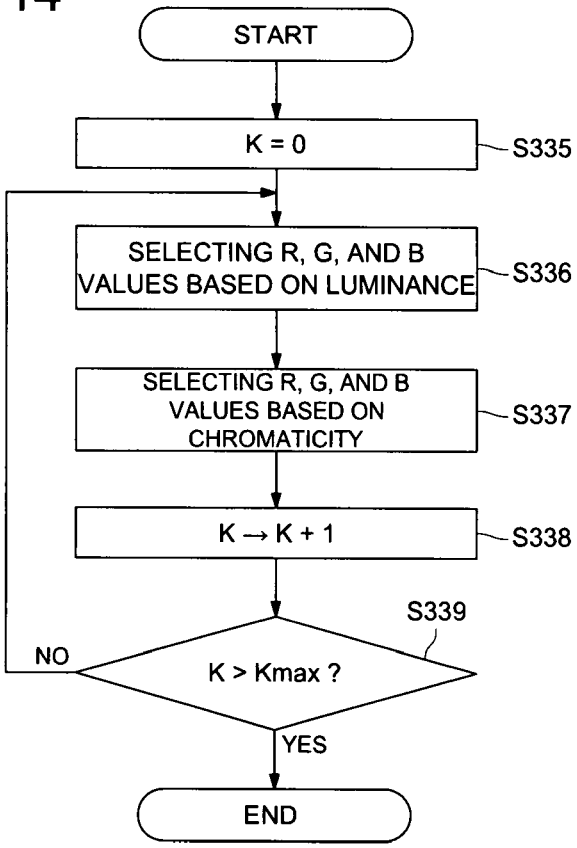
FIG. 14 shows a flowchart indicating a selecting process of R, G and B signal values in the second embodiment.

Referring to the flowchart shown in FIG. 14, the second embodiment of the operation for selecting the R, G, and B values, to be conducted in Step S33 shown in FIG. 6, will be detailed in the following. As shown in FIG. 14, the second embodiment is different from the first embodiment described in the foregoing, on the point that the secondary selection based on the chromaticity is conducted successively after the primary selection based on the luminance is completed, in the signal value determining process. In the following, only the processing different from the first embodiment will be detailed.

In the second embodiment, the candidate selection section 62 selects $C \times 2^n$ ($2^{(m+1)} \leq C \leq 2^{(m+3)}$) sets of R, G, and B signal values out of all combinations ($256^3$ sets) of R, G, and B signal values represented by a 8-bit/RGB color display image data group as the candidate R, G, and B display image data.

Further, the candidate selection section 62 selects the colors residing within a range added with an offset value of ±α (α: natural number) of each of the R, G, and B signal values with respect to the each of the reference colors (excluding a color, whose signal value is smaller than zero, or is equal to or greater than $2^n$ as a result of the offset adding operation) as the candidate colors. Although α could be any natural number, it is preferable that a value of α is equal to or greater than 1 and equal to or smaller than 3, so as not to excessively increase the number of candidate colors. In this connection, it is also applicable that the value of α to be employed in the second embodiment is greater than that of the first embodiment, since the two stage selections based on both the luminance and the chromaticity are conducted.

In the image display method of the second embodiment, the target luminance setting section 64 determines a target luminance Y (k) for the internal signal value k=0 in the signal value determining process (Step S335). After that, the luminance calculation section 66 calculates the luminance of each of the candidate colors by employing the equation (1) aforementioned (luminance calculation process). Then, the signal value decision section 67 primarily selects a plurality of candidate colors A to C (primary RGB display image data) nearest to the target luminance Y (k) (Step S336, luminance selection process). In this connection, in the second embodiment, although the number of the primary RGB display image data to be selected in the primary selection is set at 3, the number of the primary RGB display image data can be changed as needed, without setting any limitation for it.

Next, the chromaticity calculation section 65, for the respective candidate colors A to C, calculates the color stimulus values X, Y, and Z using the general Formula (1) and obtains the chromaticity on the basis of the color stimulus values calculated (the chromaticity calculation process). Here, the chromaticity (L*, a*, b*) is generally a CIE L*a*b* color specification system, which serves as the uniform color space and is indicated by using the color stimulus values X, Y, and Z and the equations (4) to (6) indicated as follows.

$$L^* = 116(Y/Yo)^{\frac{1}{3}} - 16 \quad (4)$$

$$a^* = 500\{(X/Xo)^{\frac{1}{3}} - (Y/Yo)^{\frac{1}{3}}\} \quad (5)$$

$$b^* = 200\{(Y/Yo)^{\frac{1}{3}} - (Z/Zo)^{\frac{1}{3}}\} \quad (6)$$

Further, the target chromaticity decision section 63 assumes the chromaticity of the R, G, and B values selected for the internal signal value (k−1) of the monochromatic image data as target chromaticity. And, the signal value decision section 67 obtains a color difference ΔE*ab (k−1) in the CIE L*a*b* color specification system between the target chromaticity obtained in this way and the estimated chromaticity of the candidate colors A to C and selects secondarily a color having a minimum |ΔE*ab (k−1)| among the candidate colors A to C as a selection color (Step S337). For example, as shown in FIG. 12, when the estimated chromaticity of the candidate color A is nearest to the target chromaticity, the candidate color A is a selection color. Further, the R, G, and B values of the selection color are set to correspondence as the R, G, and B display image data.

The color difference ΔE*ab (k−1) in the CIE L*a*b* color specification system is defined by the equation (7) indicated below, though it may be defined as Formula (8) excluding the influence of an index L* corresponding to the luminance.

$$\Delta E^*ab = \{(\Delta L^*)^2 + (\Delta a^*)^2 + (\Delta b^*)^2\}^{\frac{1}{2}} \quad (7)$$

$$\Delta E^*ab = \{(\Delta a^*)^2 + (\Delta b^*)^2\}^{\frac{1}{2}} \quad (8)$$

Namely, in Step S337, the chromaticity of the R, G, and B display image data corresponding to the monochromatic image data of the internal signal value k−1 is assumed as a target chromaticity. And, the chromaticity selection process, among the primary candidate R, G, and B display image data corresponding to the monochromatic image data of the internal signal value k, selects the R, G, and B display image data of the chromaticity having a minimum color difference from the target chromaticity, and establishes the selected R, G, and B display image data as the R, G, and B values of the internal signal value k. According to the abovementioned process, it becomes possible to suppress the chromaticity variations between the R, G, and B display image data of the continuous internal signal value k, and accordingly, when looking at the liquid crystal panel 2 at an ordinary observation capacity, as a whole, the grayscale continuity of chromaticity can be stabilized.

Figure 15:
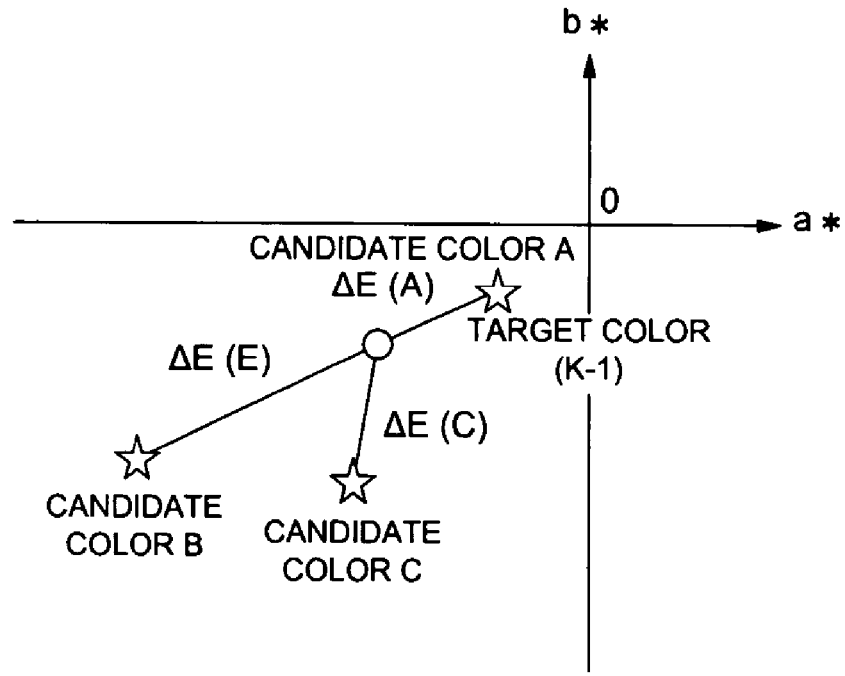
FIG. 15 shows an explanatory view indicating a selecting operation of a selected color based on chromaticity in the second embodiment.
Figure 16:
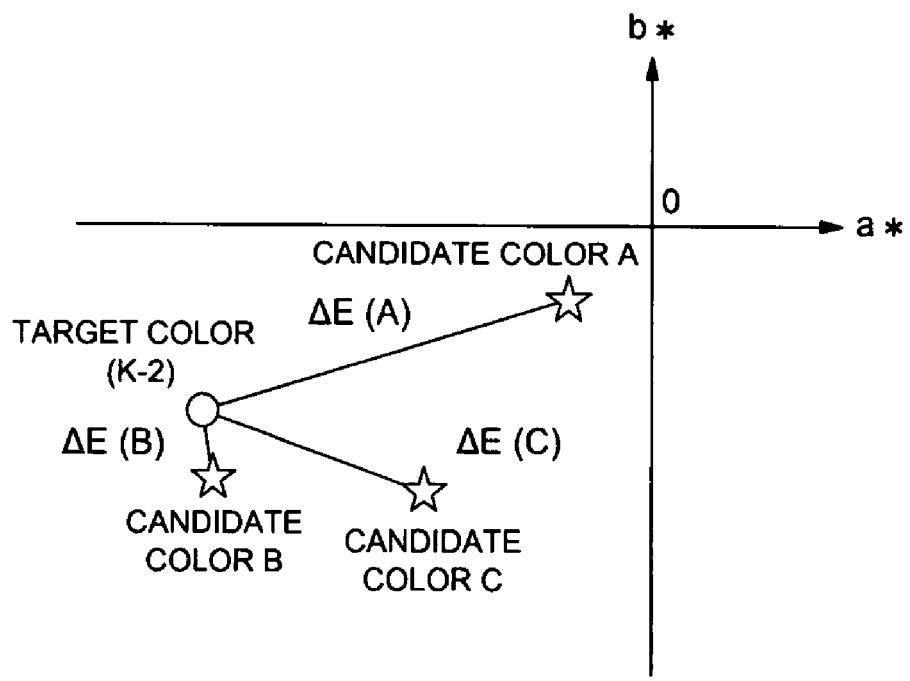
FIG. 16 shows an explanatory view indicating a selecting operation of a selected color based on chromaticity in the second embodiment.

Further, the number of target chromaticities used in Step S337 is not restricted particularly. For example, the target chromaticity corresponding to the monochromatic image data of the internal signal value k is assumed as the chromaticity of the R, G, and B display image data corresponding to the monochromatic image data of the internal signal value k−1 and the chromaticity of the R, G, and B display image data corresponding to the monochromatic image data of the internal signal value k−2 (refer to FIGS. 15 and 16). Further, among the primary candidate R, G, and B display image data corresponding to the monochromatic image data of the internal signal value k, the color difference from the chromaticity of the R, G, and B display image data corresponding to the monochromatic image data of the internal signal value k−1 is taken as |ΔE*ab (k−1)| and the color difference from the chromaticity of the R, G, and B display image data corresponding to the monochromatic image data of the signal value k−2 is taken as |ΔE*ab (k−2)|. And, the R, G, and B display image data in which |ΔE*ab (k−1)|−|ΔE*ab (k−2)| is maximized can be selected. When the above-mentioned algorism is applied to the examples shown in FIG. 15 and FIG. 16, the candidate color B is selected. Accordingly, when selecting the R, G, and B display image data in this way, the R, G, and B display image data in which the variation in the chromaticity at the signal value of the neighboring monochromatic image data is maximized within the permissible range of a user and the R, G, and B display image data in which it is minimized are selected alternately. Accordingly, the chromaticity difference between the R, G, and B display image data corresponding to the signal value of the neighboring monochromatic image data are getting large. However, generally speaking, when looking at the liquid crystal panel 2 at an ordinary observation capacity, since the density of the adjacent pixels is higher than the special frequency being visually recognizable, the chromaticity difference between adjacent display pixels cannot be clearly recognized, but recognized as a smooth plane as a whole. Namely, it becomes possible to stabilize the gradation continuity of chromaticity, even in an image in which the low luminance portion and high luminance portion are neighboring with each other.

The LUT generation section 13 takes the R, G, and B values of the single color selected in this way as R, G, and B values corresponding to the internal signal value k. Successively, the LUT generation section 13, also for the internal signal value k+1, selects similarly the R, G, and B values (Step S338, NO at Step S339), selects the R, G, and B values for all the internal signal values of 4096 grayscales, and finishes the generation of the LUT (YES at Step S339).

As mentioned in the foregoing, according to the image display apparatus 1 embodied in the present invention as the second embodiment, it becomes possible to primarily select candidate colors having the luminance near to the preferable luminance from the candidate colors of each of the internal signal values, and successively, to select a single selected color so as to conduct generating or correcting operations of the LUT, and therefore, to employ the LUT reflecting the display characteristics of the liquid crystal panel 2. Further, since the selected color can be selected from a plurality of candidate colors corresponding to a single internal signal value, it becomes possible to increase choice of combinations of the R, G, and B values with respect to the single internal signal value. Accordingly, it becomes possible not only to achieve the multi-gradation display, whose gradation characteristics exceed that of the liquid crystal panel 2, but also to make the liquid crystal panel 2 display an image having a high gradation resolution capability.

EXAMPLES

By displaying various images, represented by 10-bit through 13-bit monochromatic image data, on an image display apparatus for displaying a color image represented by 8-bit color display image data, the visual evaluation of the displayed images was conducted. The target color of the monochromatic image to be displayed is set at a blue base color being similar to that of a film image, as represented by the equation (9) shown below. In this connection, the target color is given as a model solution for determining the selected color, and a number of target colors is smaller that that of selected colors.

$$\begin{cases} R(k) = Int(k*230/255) \\ G(k) = Int(k*245/255) \\ B(k) = k \end{cases} \quad (9)$$

According to the present invention, the candidate selection section 62 selects the candidate colors from the displayable colors so that the candidate colors includes the target color and its adjacent colors, and then, the signal value decision section 67 determines an optimum selected color among the candidate colors. The adjacent color is defined as such a color, whose signal value difference relative to the target color is small, and is each of colors included in the cubic shaped lattice in which the target color is put at its central position. Although there is no specific limitation for the signal value difference of the adjacent color relative to the target color, the signal value difference is set at ±2 in FIG. 3.

Further, in each of the examples shown in the following, the candidate colors includes the target color and the adjacent colors, and a single selected color is determined among from $C \times 2^n$ candidate colors. Hereinafter, the range of "C" is defined as $1 \leq C \leq 480$. Concretely speaking, when n=8 and C=1, the number of candidate colors is 256, resulting in the same as the conventional example in which R, G, and B signal values are equivalent to each other. Further, when n=8 and C=65536, resulting in the same as the conventional example in which the selected color is directly determined among from all of the displayable colors.

Example 1

In the first example, the LUT is generated according to the correlation establishing process of the first embodiment. By applying the aforementioned LUT processing to the 13-bit/1-channel grayscale image data resulting in 1-pixel/step, grayscale image data including RGB nonequivalent colors are generated so as to display an image represented by the generated grayscale image data on the liquid crystal panel (Medical Color LCD, RadiForce R22-5, RGB 3 channels, DDL 256 gradation steps, manufactured by Nanao, Co. Ltd.). At the same time, the Photoshop 7.0 manufactured by Adobe, Co. Ltd. is employed as the image displaying software, to display the 100% image in which 1 step width is set at 0.27 mm. Since the image sizes are the same irrespective of the number of gradation steps, 8-bit display, 10-bit display, 12-bit display and 13-bit display substantially result in 32-pixels/step, 8-pixels/step, 2-pixels/step and 1-pixel/step, respectively. In addition, the employed grayscale is categorized in the middle luminance range (DDL=about 128).

The visual evaluation was conducted by viewing the displayed image from a position being apart from the screen of the liquid crystal panel by the distance of 50 cm. In the visual evaluation, the three evaluators conducted the three-stage evaluation of the displayed image from the viewpoints of luminance gradation smoothness and color unevenness. The evaluation results are indicated in Table 1 shown below.

TABLE 1

| (1) When n = 8, m = 2 | | | | | | | | | | | | | | |
|---|---|---|---|---|---|---|---|---|---|---|---|---|---|---|
| C | 1 | 2 | 4 | 8 | 12 | 16 | 24 | 32 | 48 | 64 | 80 | 160 | 240 | 320 | 480 |
| Evaluator A | 2 | 2 | 2 | 3 | 3 | 3 | 3 | 3 | 2 | 1 | 1 | 1 | 1 | 1 | 1 |
| Evaluator B | 2 | 2 | 2 | 2 | 3 | 3 | 3 | 3 | 2 | 1 | 1 | 1 | 1 | 1 | 1 |
| Evaluator C | 2 | 2 | 3 | 3 | 3 | 3 | 3 | 3 | 2 | 2 | 1 | 1 | 1 | 1 | 1 |
| Average | 2.0 | 2.0 | 2.3 | 2.7 | 3.0 | 3.0 | 3.0 | 3.0 | 2.0 | 1.3 | 1.0 | 1.0 | 1.0 | 1.0 | 1.0 |
| C | 1 | 2 | 4 | 8 | 12 | 16 | 20 | 24 | 48 | 64 | 80 | 160 | 240 | 320 | 480 |
| (2) When n = 8, m = 3 | | | | | | | | | | | | | | |
| Evaluator A | 2 | 2 | 2 | 2 | 2 | 3 | 3 | 3 | 3 | 3 | 2 | 2 | 1 | 1 | 1 |
| Evaluator B | 2 | 2 | 2 | 2 | 2 | 2 | 3 | 3 | 3 | 3 | 2 | 2 | 1 | 1 | 1 |
| Evaluator C | 2 | 2 | 2 | 2 | 2 | 3 | 3 | 3 | 3 | 3 | 2 | 2 | 1 | 1 | 1 |
| Average | 2.0 | 2.0 | 2.0 | 2.0 | 2.0 | 2.7 | 3.0 | 3.0 | 3.0 | 3.0 | 2.0 | 2.0 | 1.0 | 1.0 | 1.0 |

TABLE 1-continued (3) When n = 8, m = 4

| | | | | | | | | | | | | | | | |
|---|---|---|---|---|---|---|---|---|---|---|---|---|---|---|---|
| Evaluator A | 1 | 2 | 2 | 2 | 2 | 2 | 2 | 2 | 3 | 3 | 3 | 2 | 2 | 1 | 1 |
| Evaluator B | 1 | 2 | 2 | 2 | 2 | 2 | 2 | 2 | 3 | 3 | 3 | 3 | 2 | 1 | 1 |
| Evaluator C | 1 | 2 | 2 | 2 | 2 | 2 | 2 | 3 | 3 | 3 | 3 | 3 | 2 | 1 | 1 |
| Average | 2.0 | 2.0 | 2.0 | 2.0 | 2.0 | 2.0 | 2.0 | 2.3 | 3.0 | 3.0 | 3.0 | 2.7 | 2.0 | 1.0 | 1.0 |

(4) When n = 8, m = 5

| | | | | | | | | | | | | | | | |
|---|---|---|---|---|---|---|---|---|---|---|---|---|---|---|---|
| Evaluator A | 1 | 1 | 1 | 1 | 2 | 2 | 2 | 2 | 2 | 2 | 3 | 3 | 3 | 3 | 2 |
| Evaluator B | 1 | 1 | 1 | 1 | 1 | 2 | 2 | 2 | 2 | 2 | 3 | 3 | 3 | 2 | 2 |
| Evaluator C | 1 | 1 | 1 | 1 | 2 | 2 | 2 | 2 | 2 | 2 | 3 | 3 | 3 | 2 | 2 |
| Average | 1.0 | 1.0 | 1.0 | 1.0 | 1.7 | 2.0 | 2.0 | 2.0 | 2.0 | 2.0 | 3.0 | 3.0 | 3.0 | 2.3 | 2.0 |

Figure 17:
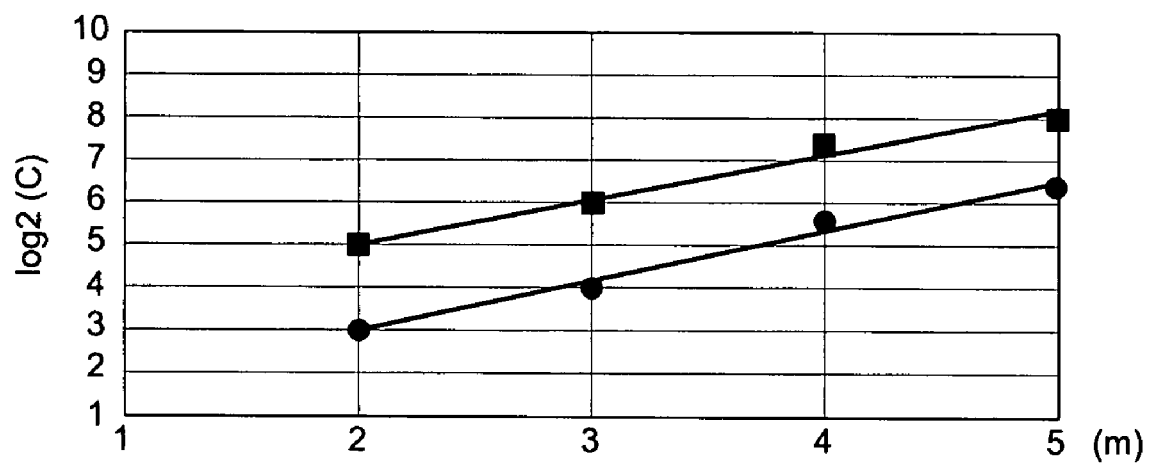
FIG. 17 shows a graph indicating evaluation results in the first embodiment.

3: luminance gradation is smooth and no color unevenness is visible
2: luminance gradation is smooth, but color unevenness is visible
2: luminance gradation is unsmooth, but no color unevenness is visible
1: luminance gradation is unsmooth and color unevenness is visible An average value of evaluation values, presented by the three evaluators, was calculated, and a border value, at which the average value is equal to or greater than 2.5 corresponding to each of the "m" values, was found. The border values found in the above are indicated in Table 2, while the graphs of them are shown in FIG. 17.

TABLE 2

| m | 2 | 3 | 4 | 5 |
|---|---|---|---|---|
| Border value at which average value is equal to or greater than 2.5 (lower limit) | | | | |
| C | 8.0 | 16.0 | 48.0 | 80.0 |
| log2(C) | 3.0 | 4.0 | 5.6 | 6.3 |
| Border value at which average value is equal to or greater than 2.5 (upper limit) | | | | |
| C | 32.0 | 64.0 | 160.0 | 240.0 |
| log2(C) | 5.0 | 6.0 | 7.3 | 7.9 |

Herein, in principle, the more the number of displayable color display image data is, the more appropriate the determined combination of R, G, and B values becomes, but on the other hand, there has been such a problem that the probability of selecting an optimum color would also decrease, resulting in a deterioration of the gradation characteristics. According to the first example embodied in the present invention, however, since the candidate colors are selected in advance from an innumerable number of displayable color display image data so as to select the selected color from the candidate colors, it becomes possible to determine an optimum combination of R, G, and B values.

Further, as shown in FIG. 17, a preferable range of the number of candidate colors can be found by the fact that the evaluation result is good when an equation (10) shown below is fulfilled.

$$2^{(m+1)} \leq C \leq 2^{(m+3)} \quad (10)$$

Example 2

In the second example, the LUT is generated according to the correlation establishing process of the second embodiment. By applying the aforementioned LUT processing to the 13-bit/1-channel grayscale image data resulting in 1-pixel/step, grayscale image data including RGB nonequivalent colors are generated so as to display an image represented by the generated grayscale image data on the liquid crystal panel in the same way as mentioned in the first example. The visual evaluation was conducted in the same way as mentioned in the first example. The evaluation results are indicated in Table 3 shown below.

TABLE 3

(1) When n = 8, m = 2

| C | 1 | 2 | 4 | 8 | 12 | 16 | 24 | 32 | 48 | 64 | 80 | 160 | 240 | 320 | 480 |
|---|---|---|---|---|---|---|---|---|---|---|---|---|---|---|---|
| Evaluator A | 2 | 2 | 2 | 3 | 3 | 3 | 3 | 3 | 3 | 3 | 3 | 2 | 2 | 2 | 2 |
| Evaluator B | 2 | 2 | 2 | 2 | 3 | 3 | 3 | 3 | 3 | 3 | 2 | 2 | 2 | 2 | 1 |
| Evaluator C | 2 | 2 | 3 | 3 | 3 | 3 | 3 | 3 | 3 | 3 | 2 | 2 | 2 | 2 | 2 |
| Average | 2.0 | 2.0 | 2.3 | 2.7 | 3.0 | 3.0 | 3.0 | 3.0 | 3.0 | 3.0 | 2.3 | 2.0 | 2.0 | 2.0 | 1.7 |

| C | 1 | 2 | 4 | 8 | 12 | 16 | 20 | 24 | 48 | 64 | 80 | 160 | 240 | 320 | 480 |
|---|---|---|---|---|---|---|---|---|---|---|---|---|---|---|---|

(2) When n = 8, m = 3

| | | | | | | | | | | | | | | | |
|---|---|---|---|---|---|---|---|---|---|---|---|---|---|---|---|
| Evaluator A | 2 | 2 | 2 | 2 | 2 | 3 | 3 | 3 | 3 | 3 | 3 | 3 | 2 | 2 | 2 |
| Evaluator B | 2 | 2 | 2 | 2 | 2 | 2 | 3 | 3 | 3 | 3 | 3 | 2 | 2 | 2 | 2 |
| Evaluator C | 2 | 2 | 2 | 2 | 2 | 3 | 3 | 3 | 3 | 3 | 3 | 3 | 2 | 2 | 2 |
| Average | 2.0 | 2.0 | 2.0 | 2.0 | 2.0 | 2.7 | 3.0 | 3.0 | 3.0 | 3.0 | 3.0 | 2.7 | 2.0 | 2.0 | 2.0 |

(3) When n = 8, m = 4

| | | | | | | | | | | | | | | | |
|---|---|---|---|---|---|---|---|---|---|---|---|---|---|---|---|
| Evaluator A | 1 | 2 | 2 | 2 | 2 | 2 | 2 | 3 | 3 | 2 | 3 | 3 | 2 | 2 |
| Evaluator B | 1 | 2 | 2 | 2 | 2 | 2 | 2 | 2 | 3 | 3 | 2 | 3 | 3 | 3 | 2 |
| Evaluator C | 1 | 2 | 2 | 2 | 2 | 2 | 2 | 3 | 3 | 2 | 3 | 3 | 3 | 3 |
| Average | 2.0 | 2.0 | 2.0 | 2.0 | 2.0 | 2.0 | 2.0 | 2.3 | 3.0 | 3.0 | 2.0 | 3.0 | 3.0 | 2.7 | 2.3 |

TABLE 3-continued (4) When n = 8, m = 5

| | | | | | | | | | | | | | | | |
|---|---|---|---|---|---|---|---|---|---|---|---|---|---|---|---|
| Evaluator A | 1 | 1 | 1 | 1 | 2 | 2 | 2 | 2 | 2 | 2 | 3 | 3 | 3 | 3 | 3 |
| Evaluator B | 1 | 1 | 1 | 1 | 1 | 2 | 2 | 2 | 2 | 2 | 3 | 3 | 3 | 3 | 3 |
| Evaluator C | 1 | 1 | 1 | 1 | 2 | 2 | 2 | 2 | 2 | 2 | 3 | 3 | 3 | 3 | 3 |
| Average | 1.0 | 1.0 | 1.0 | 1.0 | 1.7 | 2.0 | 2.0 | 2.0 | 2.0 | 2.0 | 3.0 | 3.0 | 3.0 | 3.0 | 3.0 |

Figure 18:
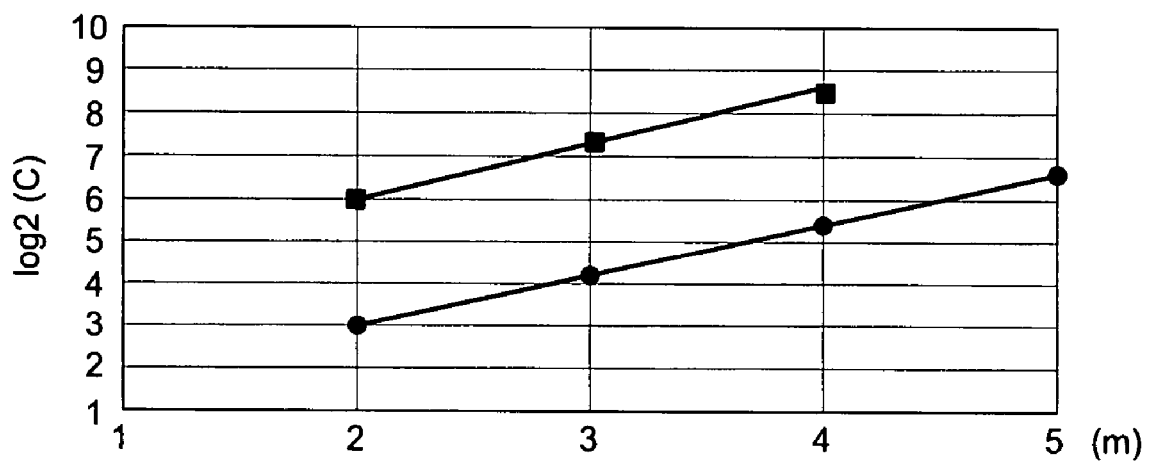
FIG. 18 shows a graph indicating evaluation results in the second embodiment.

3: luminance gradation is smooth and no color unevenness is visible
2: luminance gradation is smooth, but color unevenness is visible
2: luminance gradation is unsmooth, but no color unevenness is visible
1: luminance gradation is unsmooth and color unevenness is visible An average value of evaluation values, presented by the three evaluators, was calculated, and a border value, at which the average value is equal to or greater than 2.5 corresponding to each of the "m" values, was found. The border values found in the above are indicated in Table 4, while the graphs of them are shown in FIG. 18.

TABLE 4

| m | 2 | 3 | 4 | 5 |
|---|---|---|---|---|
| Border value at which average value is equal to or greater than 2.5 (lower limit) | | | | |
| C | 8.0 | 16.0 | 48.0 | 80.0 |
| log2(C) | 3.0 | 4.0 | 5.6 | 6.3 |
| Border value at which average value is equal to or greater than 2.5 (upper limit) | | | | |
| C | 64.0 | 160.0 | 320.0 | — |
| log2(C) | 6.0 | 7.3 | 8.3 | — |

According to the second example embodied in the present invention, as well as the first example, since the candidate colors are selected in advance from an innumerable number of displayable color display image data so as to select the selected color from the candidate colors, it becomes possible to determine an optimum combination of R, G, and B values. Further, as shown in FIG. 18, a preferable range of the number of candidate colors can be found by the fact that the evaluation result is good when an equation (11) shown below is fulfilled.

$$2^{(m+1)} \leq C \leq 2^{(m+4)} \tag{11}$$

In the second embodiment, since the selected color is determined by conducting the secondary selecting operation based on the chromaticity successively after the primary selecting operation based on the luminance is completed, there exists a little danger of selecting an undesired combination of R, G, and B values, compared to the first example in which the selected color is determined by conducting the selecting operation based on the luminance only, and, in addition, the range of the number of preferable candidate colors is wider than that in the first example. Accordingly, since it is possible to increase the number of candidate colors, it becomes possible to display an image having a higher gradation number with a preferable color tone.

Incidentally, although it is assumed that n=8 in the present embodiment, it is needless to say that the same operations and effects as described in the foregoing can be achieved even when n>8. Further, although it is assumed that the 1-channel monochromatic image data are converted to the 3-channel RGB color display image data in the present embodiment, the scope of the present invention is not limited to such the 3-channel RGB color display image data, but the present invention is also applicable to a converting operation to the CMYK color display image data, etc., as needed.

Further, as a result of measuring a part of displaying results when all of the three evaluator presented point 3, it has been confirmed that every displayed color resided within the area surrounded by the lines connecting the coordinate points of (0.2, 0.275), (0.275, 0.225), (0.325, 0.4), (0.4, 0.35) on the CIE chromaticity coordinates.

According to the present invention, by selecting the candidate color display image data in advance, it becomes possible to minimize the length of the arithmetic calculation time interval. Further, by conducting the signal value determining process after selecting the candidate color display image data within a preferable range, it becomes possible not only to exclude a risk of selecting such the color display image data that exhibit undesired color tone, but also to obtain correlation with an appropriate color tone. Accordingly, even when the low-cost color image display apparatus having a relatively small number of drive gradations is employed, it becomes possible for inputted monochromatic image data having a number of gradations, which is equal to or greater than four times of the number of drive grayscales of the color image display apparatus, to display an image having sufficient gradation reproducibility and color tone for conducting a medical image diagnoses. Further, since the signal value determining process can be executed with a simple algorism, a number of conditions to be employed in the signal value determining process can be limited to a small number, and accordingly, it also becomes possible to lower the possibility of error occurrence.

While the preferred embodiments of the present invention have been described using specific term, such description is for illustrative purpose only, and it is to be understood that changes and variations may be made without departing from the spirit and scope of the appended claims.

What is claimed is:

1. An image display method for displaying an image on a color monitor, based on a n-bit color display image-data group that is represented by plural channels including three channels or more, and that is acquired by converting (n+m)-bit monochromatic image data represented by a single channel to the n-bit color display image-data group, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2, the image display method comprising:

selecting "H" sets of signal-values of the plural channels out of all combinations of signal-values of the plural channels included in the n-bit color display image-data group as candidate color display signal-value sets, wherein numeral "H" indicates a positive integer;

determining a single color display signal-value set, to be correlated with each of signal values represented by the (n+m)-bit monochromatic image data, from among the "H" sets of candidate color display signal-value sets, with respect to each of the signal values represented by the (n+m)-bit monochromatic image data; and establishing the correlation by correlating each of the signal values represented by the (n+m)-bit monochromatic image data with the color display signal-value set determined in the determining step while corresponding thereto.

2. The image display method of claim 1, further comprising:

acquiring luminance information corresponding to each of the signal values represented by the (n+m)-bit monochromatic image data;

acquiring chromaticity information corresponding to each of the signal values represented by the (n+m)-bit monochromatic image data;

wherein, in the determining step, the single color display signal-value set, which is correlated with each of the signal values represented by the (n+m)-bit monochromatic image data, is determined, based on the luminance information and the chromaticity information acquired in the acquiring steps.

3. The image display method of claim 1, wherein the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

4. The image display method of claim 1, further comprising:

selecting a desired color tone of the image to be displayed on the color monitor from a plurality of candidate color tones;

wherein the candidate color display signal-value sets are selected, so that the desired color tone corresponds to a color tone of the image to be displayed on the color monitor.

5. The image display method of claim 1, wherein numeral "H", being a number of the candidate color display signal-value sets, fulfills equations indicated as follows;

$$H = C \times 2^n$$

$$2^{(m+1)} \leq C \leq 2^{(m+4)}.$$

6. The image display method of claim 5, further comprising:

acquiring luminance information corresponding to each of the signal values represented by the (n+m)-bit monochromatic image data;

acquiring chromaticity information corresponding to each of the signal values represented by the (n+m)-bit monochromatic image data;

wherein, in the determining step, the single color display signal-value set, which is correlated with each of the signal values represented by the (n+m)-bit monochromatic image data, is determined, based on the luminance information and the chromaticity information acquired in the acquiring steps.

7. The image display method of claim 5, wherein the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

8. The image display method of claim 5, further comprising:

selecting a desired color tone of the image to be displayed on the color monitor from a plurality of candidate color tones;

wherein the candidate color display signal-value sets are selected, so that the desired color tone corresponds to a color tone of the image to be displayed on the color monitor.

9. An image display method for displaying an image on a color monitor, based on a n-bit color display image-data group that is represented by plural channels including three channels or more, and that is acquired by converting (n+m)-bit monochromatic image data represented by a single channel to the n-bit color display image-data group, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2, the image display method comprising:

selecting "H" sets of signal-values of the plural channels out of all combinations of signal-values of the plural channels included in the n-bit color display image-data group as candidate color display signal-value sets, wherein numeral "H" indicates a positive integer;

acquiring luminance information corresponding to each of the signal values represented by the (n+m)-bit monochromatic image data;

determining a single color display signal-value set, to be correlated with each of signal values represented by the (n+m)-bit monochromatic image data, from among the "H" sets of candidate color display signal-value sets, based on the luminance information, with respect to each of the signal values represented by the (n+m)-bit monochromatic image data; and establishing the correlation by correlating each of the signal values represented by the (n+m)-bit monochromatic image data with the color display signal-value set determined in the determining step while corresponding thereto.

10. The image display method of claim 9, wherein the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

11. The image display method of claim 9, further comprising:

selecting a desired color tone of the image to be displayed on the color monitor from a plurality of candidate color tones;

wherein the candidate color display signal-value sets are selected, so that the desired color tone corresponds to a color tone of the image to be displayed on the color monitor.

12. The image display method of claim 9, wherein numeral "H", being a number of the candidate color display signal-value sets, fulfills equations indicated as follows;

$$H = C \times 2^n$$

$$2^{(m+1)} \leq C \leq 2^{(m+3)}.$$

13. The image display method of claim 12,
wherein the candidate color display signal-value sets are selected in the selecting step, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

14. The image display method of claim 12, further comprising:
selecting a desired color tone of the image to be displayed on the color monitor from a plurality of candidate color tones;
wherein the candidate color display signal-value sets are selected, so that the desired color tone corresponds to a color tone of the image to be displayed on the color monitor.

15. An image display apparatus, comprising:
an image data processing section to convert (n+m)-bit monochromatic image data represented by a single channel to a n-bit color display image-data group represented by plural channels including three channels or more, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2; and
a color image display section to display a color image on it, based on the n-bit color display image-data group outputted by the image data processing section;
wherein the image data processing section includes:
a candidate selection section to select "H" sets of signal-values of the plural channels out of all combinations of signal-values of the plural channels included in the n-bit color display image-data group as candidate color display signal-value sets, wherein numeral "H" indicates a positive integer;
a signal value decision section to determine a single color display signal-value set, to be correlated with each of signal values represented by the (n+m)-bit monochromatic image data, from among the "H" sets of candidate color display signal-value sets, with respect to each of the signal values represented by the (n+m)-bit monochromatic image data; and
a correlation establishing section to establish the correlation by correlating each of the signal values represented by the (n+m)-bit monochromatic image data with the color display signal-value set determined by the signal value decision section while corresponding thereto.

16. The image display apparatus of claim 15,
wherein the image data processing section further includes:
a luminance information acquiring section to acquire luminance information corresponding to each of the signal values represented by the (n+m)-bit monochromatic image data; and
a chromaticity information acquiring section to acquire chromaticity information corresponding to each of the signal values represented by the (n+m)-bit monochromatic image data; and
wherein the signal value decision section determines the single color display signal-value set, which is correlated with each of the signal values represented by the (n+m)-bit monochromatic image data, based on the luminance information and the chromaticity information, respectively acquired by the luminance information acquiring section and the chromaticity information acquiring section.

17. The image display apparatus of claim 15,
wherein the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

18. The image display apparatus of claim 15,
wherein the image data processing section further includes:
a color tone selecting section to select a desired color tone of the image, to be displayed on the color monitor, from a plurality of candidate color tones;
wherein the candidate selection section selects the candidate color display signal-value sets, so that the desired color tone corresponds to a color tone of the color image to be displayed on the color image display section.

19. The image display apparatus of claim 15,
wherein numeral "H", being a number of the candidate color display signal-value sets, fulfills equations indicated as follows;

$$H = C \times 2^n$$

$$2^{(m+1)} \leq C \leq 2^{(m+4)}.$$

20. The image display apparatus of claim 19,
wherein the image data processing section further includes:
a luminance information acquiring section to acquire luminance information corresponding to each of the signal values represented by the (n+m)-bit monochromatic image data; and
a chromaticity information acquiring section to acquire chromaticity information corresponding to each of the signal values represented by the (n+m)-bit monochromatic image data; and
wherein the signal value decision section determines the single color display signal-value set, which is correlated with each of the signal values represented by the (n+m)-bit monochromatic image data, based on the luminance information and the chromaticity information, respectively acquired by the luminance information acquiring section and the chromaticity information acquiring section.

21. The image display apparatus of claim 19,
wherein the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

22. The image display apparatus of claim 19,
wherein the image data processing section further includes:
a color tone selecting section to select a desired color tone of the image, to be displayed on the color monitor, from a plurality of candidate color tones;
wherein the candidate selection section selects the candidate color display signal-value sets, so that the desired color tone corresponds to a color tone of the color image to be displayed on the color image display section.

23. An image display apparatus, comprising:

an image data processing section to convert (n+m)-bit monochromatic image data represented by a single channel to a n-bit color display image-data group represented by plural channels including three channels or more, based on a correlation established in advance between the (n+m)-bit monochromatic image data and the n-bit color display image-data group, wherein numeral "n" indicates a positive integer equal to or greater than 8, while numeral "m" indicates a positive integer equal to or greater than 2; and a color image display section to display a color image on it, based on the n-bit color display image-data group outputted by the image data processing section;

wherein the image data processing section includes:
- a candidate selection section to select "H" sets of signal-values of the plural channels out of all combinations of signal-values of the plural channels included in the n-bit color display image-data group as candidate color display signal-value sets, wherein numeral "H" indicates a positive integer;
- a luminance information acquiring section to acquire luminance information corresponding to each of the signal values represented by the (n+m)-bit monochromatic image data;
- a signal value decision section to determine a single color display signal-value set, to be correlated with each of signal values represented by the (n+m)-bit monochromatic image data, from among the "H" sets of candidate color display signal-value sets, based on the luminance information acquired by the luminance information acquiring section, with respect to each of the signal values represented by the (n+m)-bit monochromatic image data; and
- a correlation establishing section to establish the correlation by correlating each of the signal values represented by the (n+m)-bit monochromatic image data with the color display signal-value set determined by the signal value decision section while corresponding thereto.

24. The image display apparatus of claim 23, wherein the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

25. The image display apparatus of claim 23, wherein the image data processing section further includes:

a color tone selecting section to select a desired color tone of the image, to be displayed on the color monitor, from a plurality of candidate color tones;

wherein the candidate selection section selects the candidate color display signal-value sets, so that the desired color tone corresponds to a color tone of the color image to be displayed on the color image display section.

26. The image display apparatus of claim 23, wherein numeral "H", being a number of the candidate color display signal-value sets, fulfills equations indicated as follows;

$$H = C \times 2^n$$

$$2^{(m+1)} \leq C \leq 2^{(m+3)}.$$

27. The image display apparatus of claim 26, wherein the candidate selection section selects the candidate color display signal-value sets, so that each of coordinate points, indicated by each of the candidate color display signal-value sets on CIE chromaticity coordinates (x, y), resides within an area surrounded by lines connecting points of (0.2, 0.275), (0.275, 0.225), (0.325, 0.4), (0.4, 0.35) on the CIE chromaticity coordinates (x, y).

28. The image display apparatus of claim 26, wherein the image data processing section further includes:

a color tone selecting section to select a desired color tone of the image, to be displayed on the color monitor, from a plurality of candidate color tones;

wherein the candidate selection section selects the candidate color display signal-value sets, so that the desired color tone corresponds to a color tone of the color image to be displayed on the color image display section.

* * * * *